(12) United States Patent
Gilbert et al.

(10) Patent No.: US 11,238,956 B2
(45) Date of Patent: Feb. 1, 2022

(54) METHODS OF IDENTIFYING CELLULAR REPLICATION TIMING SIGNATURES AND METHODS OF USE THEREOF

(71) Applicant: Florida State University Research Foundation, Inc., Tallahassee, FL (US)

(72) Inventors: David M. Gilbert, Tallahassee, FL (US); Juan Carlos Rivera-Mulia, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 1125 days.

(21) Appl. No.: 15/615,069

(22) Filed: Jun. 6, 2017

(65) Prior Publication Data
US 2017/0351808 A1  Dec. 7, 2017

Related U.S. Application Data

(60) Provisional application No. 62/346,619, filed on Jun. 7, 2016.

(51) Int. Cl.
| | |
|---|---|
| *G16B 20/20* | (2019.01) |
| *G16B 20/00* | (2019.01) |
| *G16B 25/00* | (2019.01) |
| *G16B 40/30* | (2019.01) |
| *G16B 25/10* | (2019.01) |
| *G16B 40/00* | (2019.01) |
| *G16B 30/00* | (2019.01) |

(52) U.S. Cl.
CPC ............ *G16B 20/20* (2019.02); *G16B 20/00* (2019.02); *G16B 25/00* (2019.02); *G16B 25/10* (2019.02); *G16B 40/30* (2019.02); *G16B 30/00* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 8,725,423 B2 | 5/2014 | Gilbert et al. | |
| 8,728,979 B2 | 5/2014 | Gilbert et al. | |
| 9,245,090 B2 | 1/2016 | Gilbert et al. | |
| 2009/0062140 A1* | 3/2009 | Gilbert | C12Q 1/6804 506/9 |
| 2012/0322675 A1 | 12/2012 | Gilbert et al. | |
| 2013/0184998 A1* | 7/2013 | Gilbert | G16B 45/00 702/19 |
| 2014/0149048 A1* | 5/2014 | Gilbert | G16B 40/00 702/20 |
| 2014/0243221 A1* | 8/2014 | Gilbert | C12Q 1/6804 506/8 |
| 2015/0203907 A1 | 7/2015 | Gilbert et al. | |
| 2016/0378915 A1* | 12/2016 | Araya | G16B 30/00 702/20 |
| 2019/0005191 A1* | 1/2019 | Hnisz | C12Q 1/6886 |

OTHER PUBLICATIONS

Koren et al. in Cell (2014) vol. 159:1015-1026.*
Liu et al. in Bioinformatics (2016) vol. 32(5):641-649.*
Lu et al. in Cell Reports (2014) vol. 7:70-78.*
Pope et al. in Chromosome Research (2010) vol. 18:127-136.*
Pope et al. in Nature (2014) vol. 515:16 pages.*
Rivera-Mulia et al. in Genome Research (2015) vol. 25:1091-1103.*
Rivera-Mulia et al. in Current Opinion in Cell Biology (2016) vol. 40:168-178.*
Rivera-Mulia et al. in PNAS (2017) Published online on Dec. 1, 2017:E10972-10980.*
Weddington et al. in BMC Bioinformatics (2008) vol. 9:11 pages.*
Ryba et al.: "Genome-Scale Analysis of Replication Timing from Bench to Bioinformatics", Nat Protoc. Jun. 2011, 6(6): 870-895.

* cited by examiner

*Primary Examiner* — Lori A. Clow
(74) *Attorney, Agent, or Firm* — Fox Rothschild LLP

(57) ABSTRACT

Methods for identifying and classifying differences between biological samples are based on replication timing (RT) data. By comparing RT data for a test sample(s) to RT data for already characterized samples, one can identify differences and profile any new cell type or disease. These new methods allow for the detection of all the changes between distinct samples, many of which would escape detection by previous methods that discard any features showing any intra-sample variation.

11 Claims, 32 Drawing Sheets

FIG. 2A
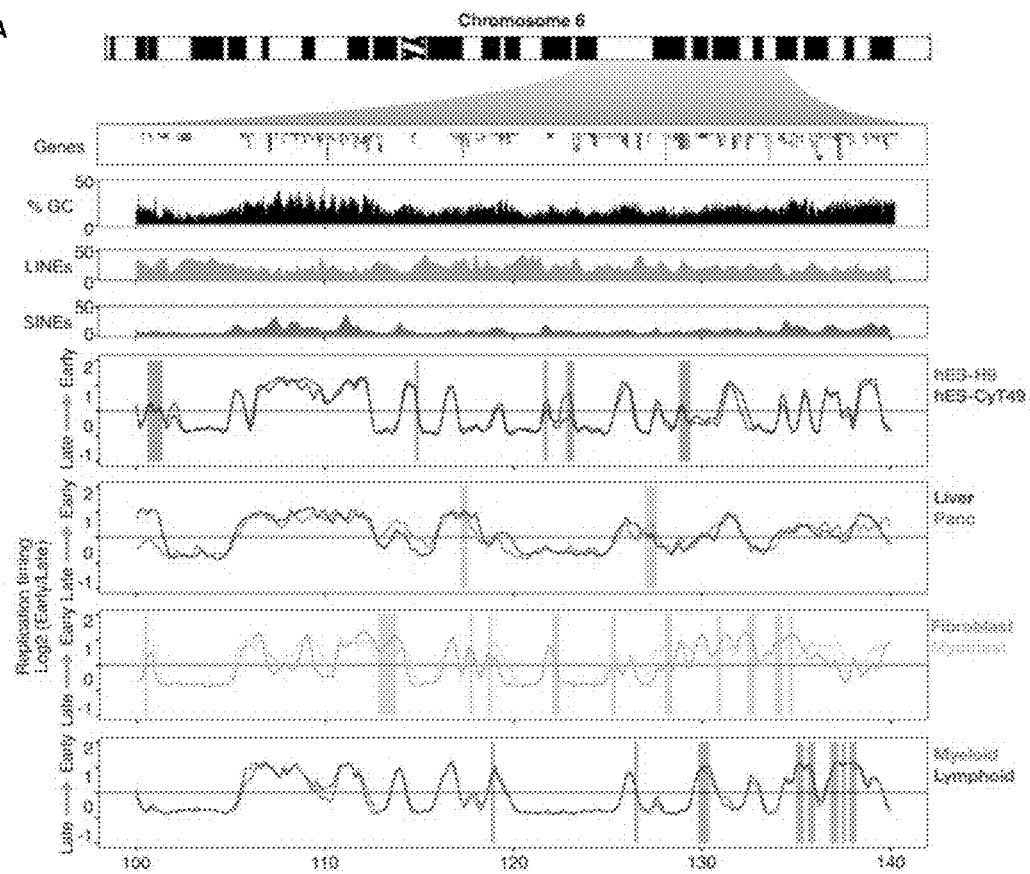
FIG. 2B
FIG. 2C
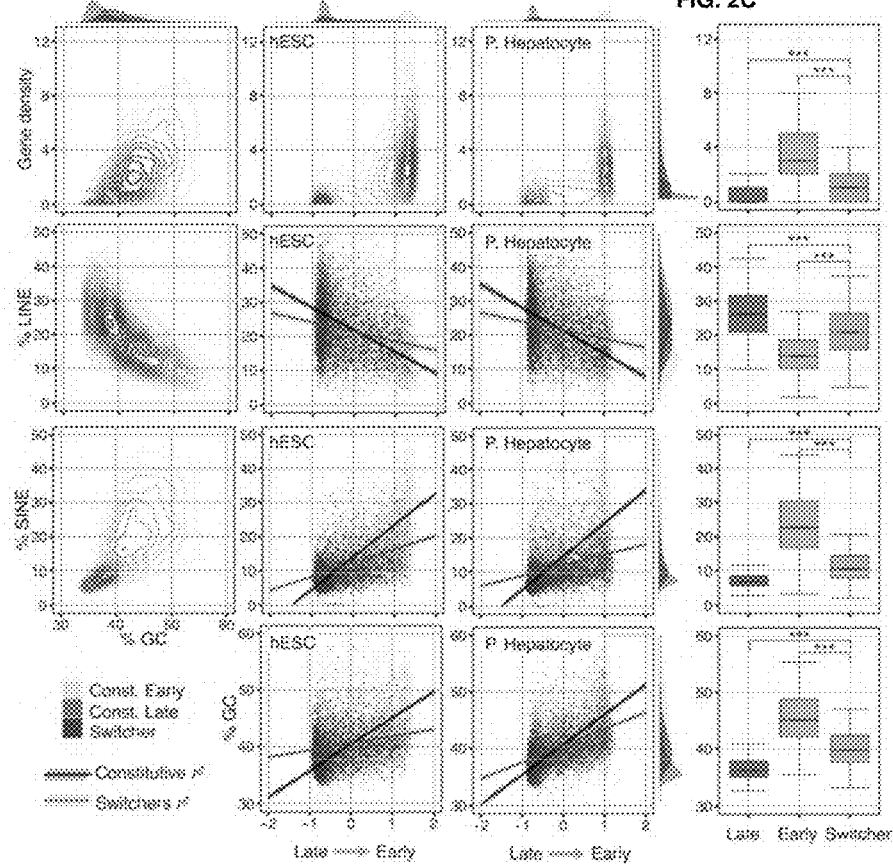

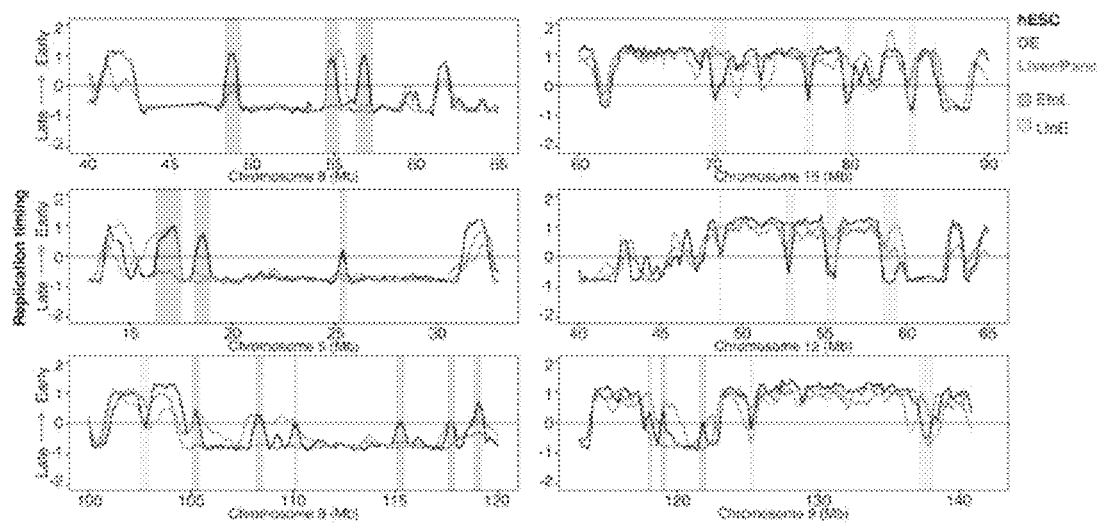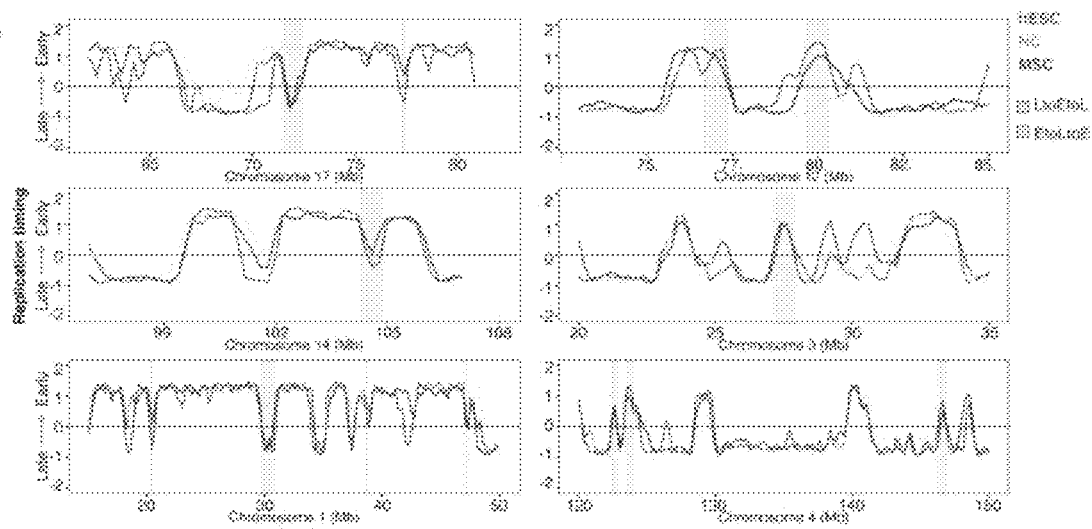

FIG. 4B
Endoderm

FIG. 4C
Mesoderm

FIG. 4D
Ectoderm

FIG. 6A
|  | EtoL changes | | | LtoE changes | | |
|---|---|---|---|---|---|---|
|  | expressed when Early | expressed when Late | expressed after switch | expressed when Late | expressed when Early | expressed before switch |
| All | 46% | 39% | 84% | 39% | 39% | 77% |
| C-class | 83% | 78% | 92% | 68% | 81% | 84% |
| E-class | 21% | 0% | 0% | 0% | 17% | 0% |
| L-class | 0% | 0% | -- | 0% | 0% | -- |
| N-class | 0% | 0% | -- | 0% | 0% | -- |
FIG. 6B
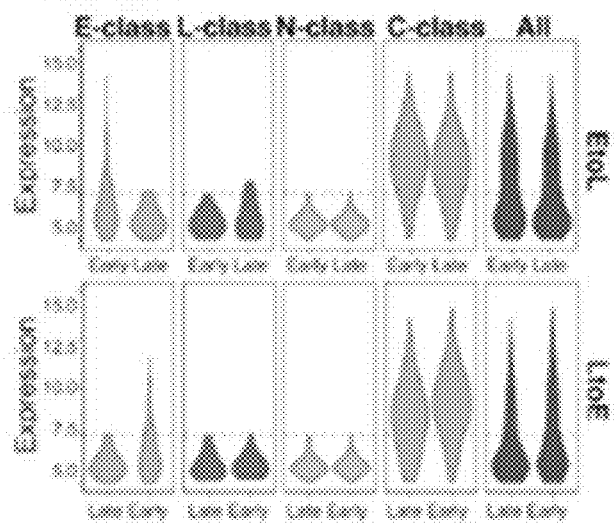
FIG. 6C
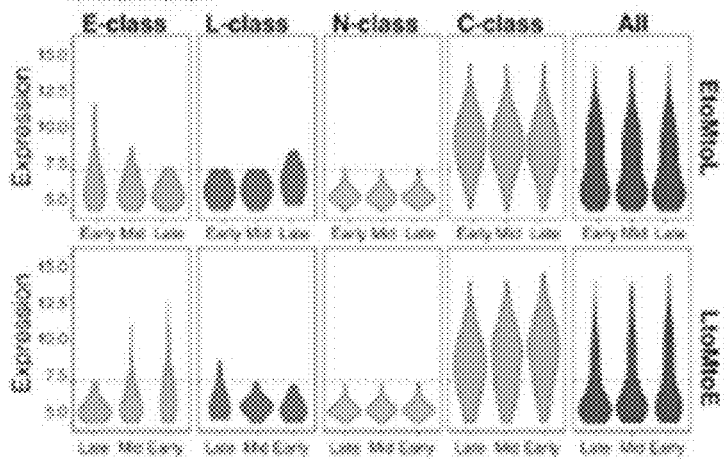

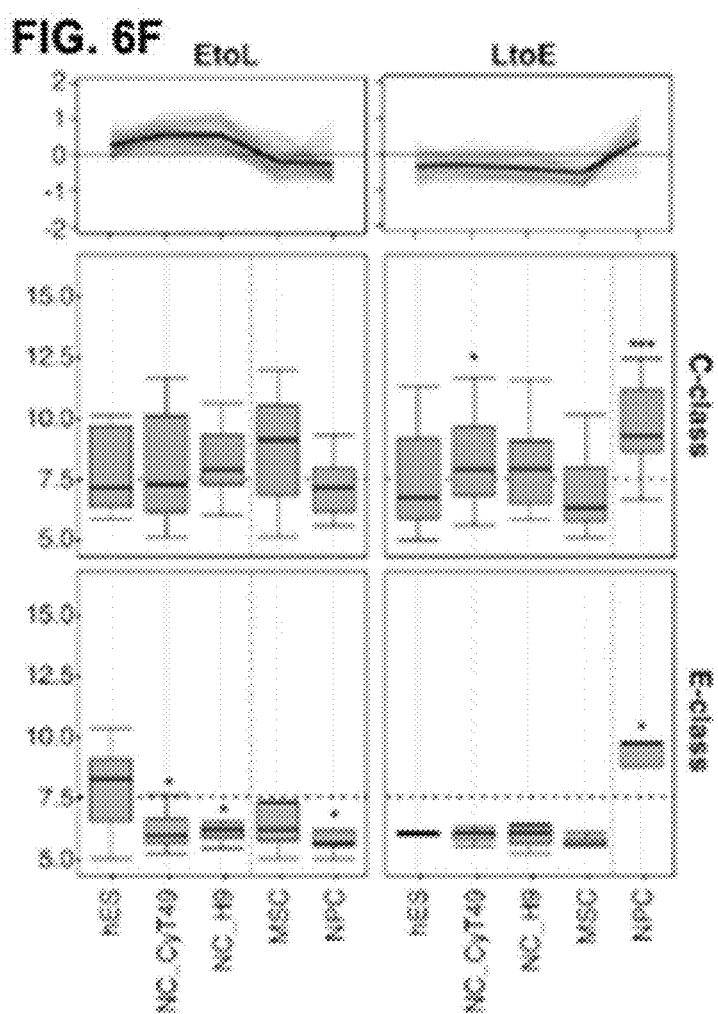

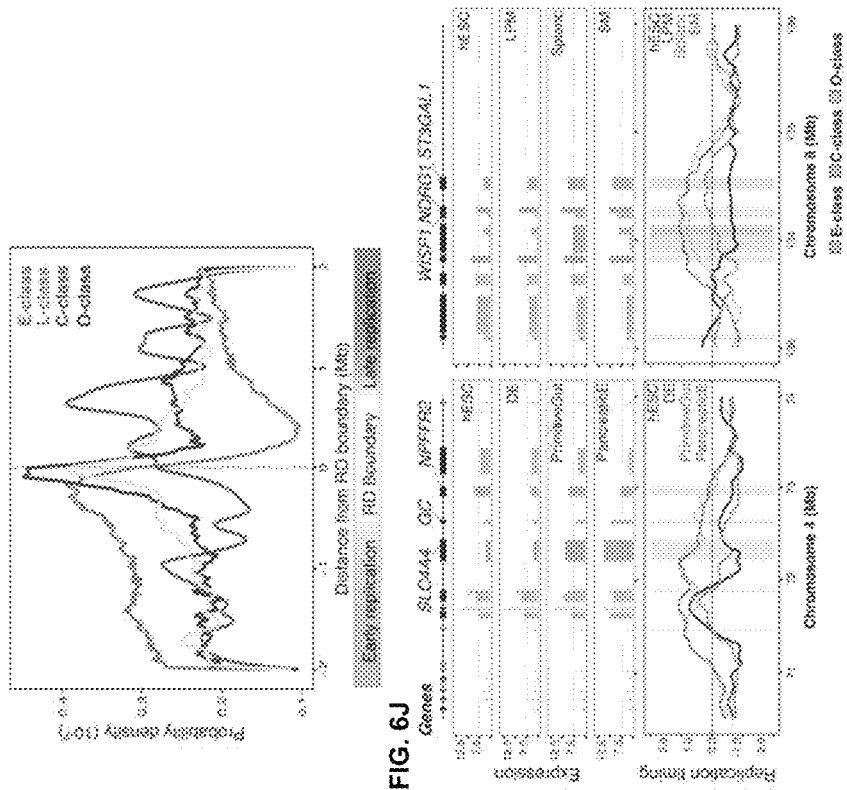
FIG. 6I
FIG. 6J
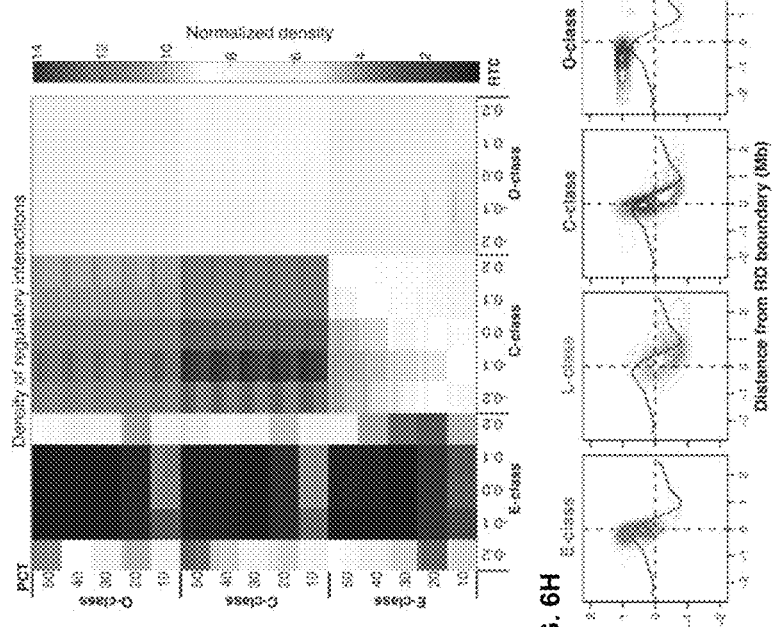
FIG. 6G
FIG. 6H

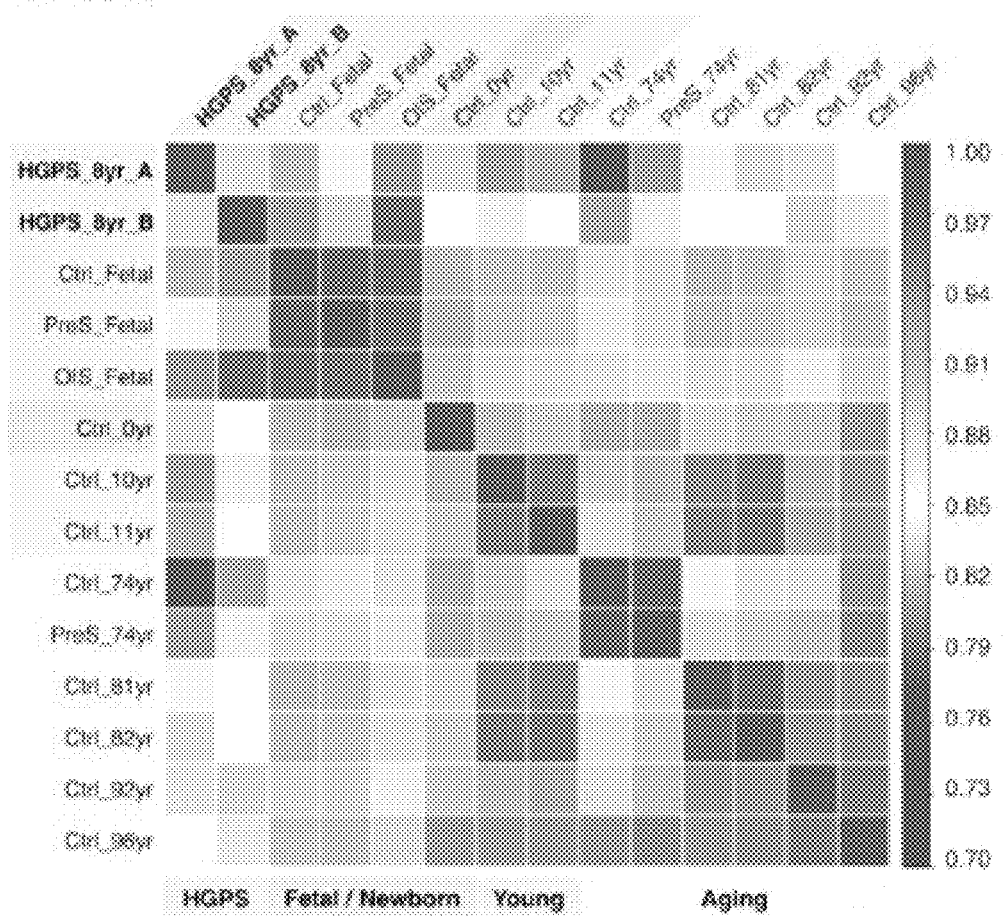

METHODS OF IDENTIFYING CELLULAR REPLICATION TIMING SIGNATURES AND METHODS OF USE THEREOF

CROSS-REFERENCE TO RELATED APPLICATION

This application claims priority to U.S. Provisional Patent Application No. 62/346,619, filed Jun. 7, 2016, which is incorporated herein by reference in its entirety.

FEDERALLY SPONSORED RESEARCH

This invention was made with government support under grant no. GM083337, awarded by the National Institutes of Health. The Government has certain rights in the invention.

FIELD OF THE INVENTION

The invention relates to the fields of genomics, molecular biology and medicine. More particularly, the invention relates to methods for identifying cell type-specific and disease-specific replication timing (RT) signatures.

BACKGROUND

All eukaryotes duplicate their genomes in a defined temporal order known as the replication-timing (RT) program (Hiratani et al. Curr Opin Genet Dev 19: 142-149 (2009); Pope and Gilbert J Mol Biol 425: 4690-4695 (2013)). Proper regulation of RT is essential for genome stability, and abnormal RT programs have been identified in cancer cells (Ryba et al. Genome Res 22: 1833-1844 (2012)). In mammals, cell fate commitment is accompanied by dynamic changes in RT in units of 400-800 kb known as replication domains (RDs) (Hiratani et al. PLoS Biol 6:e245 (2008); Hiratani et al. Genome Res 20: 155-169 (2010); Hansen et al. Proc Natl Acad Sci 107: 139-144 (2010); Ryba et al. Genome Res 20: 761-770 (2010)). RT is closely aligned with spatial organization of chromatin in the nucleus; early and late RDs reside in distinct nuclear, and cytogenetic visualization of pulse-labeled DNA synthesis reveals distinct punctate replication foci whose structure remains stable for many cell cycles. Chromatin conformation methods that map long-range chromatin interactions have revealed that chromosomes consist of topologically associating domains (TADs) that correspond to units of RT regulation, whereas the interactions between TADs form two distinct subnuclear compartments that correspond to the early and late replicating segments of the genome within any given cell type. Hence, RT constitutes a very informative functional readout of large-scale chromatin organization across distinct cell types and its regulation during development. Many approaches using distinct genome-wide data have been developed to identify and characterize the variation between different samples. However, improved methods obtaining greater information regarding specific cell lineages, identity cell of origin of a tumor, and for identifying novel biomarkers of disease are desired.

One such disease is Hutchinson-Gilford progeria syndrome (HGPS), a rare genetic disorder caused by a point mutation in the LMNA gene that encodes two of the major components of the nuclear lamina: lamin A and C. The mutation activates an alternative mRNA splicing site that results in a truncated version of the protein, referred to as progerin. Patients with HGPS display multiple anomalies including alopecia, loss of body fat, limited growth, scleroderma and cardiovascular complications that eventually lead to their premature death. At the cellular level, expression of the abnormal protein leads to the accumulation of progerin in the nuclear membrane, which is linked to multiple nuclear defects such as abnormal morphology of the nucleus, altered chromatin organization, loss of heterochromatin, deficiencies in DNA-damage response and impaired anti-oxidative pathways. Intriguingly, HGPS is one of several congenital disorders known as the progeroid syndromes that despite their similar pathophysiological symptoms arise from mutations in genes with distinct functions and display different alterations at the cellular level. For example, cells from Rothmund-Thomson syndrome (RTS), which results from a mutation in the DNA helicase Q4 (RECQL4), do not show the characteristic defects in nuclear envelope of HGPS but the patients present with similar symptoms. Thus, despite recent progress in the characterization of the cellular phenotypes associated with HGPS and related progeroid diseases, little is known about the mechanisms linking the cellular defects to the pathophysiological manifestations of the disease.

SUMMARY

Described herein are methods of identifying RT signatures for test samples and methods of using these RT signatures. The experiments described herein show that replication timing can be exploited to identify the dynamic changes in chromosome organization during development and its alterations in specific diseases. As described in the Examples below, multiple cell types derived from human stem cells were analyzed and lineage-specific RT signatures were identified. The results described herein also introduce the utility of RT signatures to identify novel biomarkers not detected by other methods. Replication timing (RT) abnormalities in cells from patients with HGPS were analyzed and a signature that distinguished HGPS from natural aging was identified, revealing a new gene marker that might be directly associated with the clinical manifestations of the progeria disease. Similarly, the methods can be used to analyze samples from any disease and compare those RT signatures with a normal control sample RT signature in order to identify disease-specific RT signatures.

The experiments described herein demonstrate the first use of RT as an epigenetic mark to discover novel markers of disease, and are the most comprehensive genome-wide comparison of progeroid diseases to natural aging. These results show the first association of abnormal RT with altered gene variant expression, identified molecular abnormalities in common between progeroid diseases that are causally linked to mutations of very different functional proteins (LNMA and RECQL4), and showed linkage of TP63 to early manifestations of progeroid disease progression.

Accordingly, described herein is method of identifying a RT signature for a test sample of cells or plurality of test samples of cells. The method includes generating a RT profile for the test sample or RT profiles for the plurality of test samples; generating a RT profile for at least one reference sample; removing pericentromeric and subtelomeric regions to remove large repetitive DNA regions from the test sample and reference sample RT profiles; dividing genomes or sub-genomic regions into about 50 to about 200 kb (e.g., 40, 45, 49, 50, 55, 60, 65, 70, 75, 80, 85, 90, 95, 100, 110, 125, 150, 175, 180, 185, 190, 199, 200, 201, 205, etc.) non-overlapping windows and averaging the RT values within each window; removing chromosome segments having invariant RT between test and reference samples resulting in a collection of remaining chromosome segments that include all variation in RT between the samples, wherein the remaining chromosome segments are variant regions; performing k-means clustering of the variant regions to identify specific patterns of RT and hierarchical clustering of all samples; when all samples are processed, defining a threshold in correlation values of the hierarchical clustering to identify groups of samples that are related by their RT; and identifying RT signatures that distinguish the test sample or plurality of test samples from the reference sample that is the set of chromosome segments whose RT best distinguishes the test sample or plurality of test samples. In some embodiments, sex chromosomes are also removed to discard gender differences. In other embodiments, for gender-associated differences, RT signatures can be identified by preserving sex chromosomes and including proper reference samples. In the method, RT signatures are the specific k-means clusters of chromosome segments that replicate differently between reference and test sample(s). For example, the specific k-means clusters are those that replicate either earlier or later in the test samples or plurality of test samples as compared with the at least one reference sample. In the method, the RT signature specific for the test sample of cells or plurality of test samples of cells identifies a set of chromosome regions whose RT can distinguish the test sample of cells or plurality of test samples of cells. The RT signature of the test sample of cells or plurality of test samples of cells can be used to identify a particular disease. The at least one reference sample and the test sample of cells or plurality of test sample of cells are typically the same cell type, and typically, the at least one reference sample is obtained from at least one individual not having the particular disease. In some methods, reference samples from a plurality of individuals not having the particular disease are analyzed. In some embodiments, the at least one reference sample is a plurality of different reference samples. The at least one reference sample (e.g., a plurality of reference samples) can be stored within (available within or from) a database (e.g., a public database). In the method, the test sample of cells or plurality of test samples of cells typically is not pre-defined, allowing discovery of novel subsets of samples distinguished by specific RT signatures. In some embodiments, the cells are human cells. In some embodiments, the test sample of cells or plurality of test samples of cells are frozen banked cells that have been cultured and expanded in patient-derived xenografted mice. RT profiles can be generated for genomes and/or sub-genomic regions. In the methods, generating a RT profile can include at least one of: array hybridization, S/G1, E/L, and sequencing.

Also described herein is a method of identifying a disease-specific RT signature. The method includes generating at least one RT signature specific for at least one test sample of diseased cells as compared to at least one non-diseased reference sample according to the method described above. In some embodiments, in the step of removing pericentromeric and subtelomeric regions, sex chromosomes are also removed to discard gender differences. In some embodiments, RT signatures are the specific k-means clusters of chromosome segments that replicate differently between reference and test sample(s). The specific k-means clusters are, for example, those that replicate either earlier or later in the at least one test sample of diseased cells as compared with the at least one non-diseased reference sample. The RT signature specific for the at least one test sample of diseased cells identifies a set of chromosome regions whose RT can distinguish the at least one test sample of diseased cells. Typically, the at least one non-diseased reference sample and the at least one test sample of diseased cells are the same cell type, and the at least one non-diseased reference sample is obtained from at least one individual not having the disease. The at least one non-diseased reference sample, for example, is available (stored within) a database (e.g., a public database). In one embodiment, the at least one test sample of diseased cells are frozen banked cells that have been cultured and expanded in patient-derived xenografted mice. Generating a RT profile typically includes at least one of: array hybridization, sequencing, S/G1, and E/L. The at least one test sample of diseased cells can be human cells.

Further described herein is a method of identifying novel disease markers. In one embodiment, a method of identifying a novel marker of a disease includes the steps of the method described above for identifying a RT signature for a test sample of cells or plurality of test samples of cells, resulting in at least one sample-specific RT signature for at least one test sample, wherein the at least one test sample is a sample of cells for a disease; and identifying and characterizing key features of the sample-specific RT signature. Key features can be identified and characterized by, for example, ontology analysis to determine whether chromosome regions within the sample-specific RT signature have been annotated with terms relevant for the at least one test sample, and a comparison of RT against other genomics data to determine the relevance of the sample-specific RT signature for the at least one test sample. In the method, the other genomics data can include, for example, at least one of: gene expression, epigenetic marks, and regulatory elements. In this method, the other genomics data may be available in a public database, or is generated, to reveal disease alterations linked to specific RT signatures. The method can further include a step wherein a potential novel marker and/or a therapeutic target for the at least one test (disease) sample can be identified within the key features of the sample-specific RT signature after ontology analysis and comparison of RT against other genomics data, as those chromosome segments with abnormal RT that can be associated with de-regulation of specific genes linked to the disease. In one embodiment, the at least one test sample includes frozen banked cells that have been cultured and expanded in patient-derived xenografted mice. The at least one reference sample and the at least one test sample are typically the same cell type, and the at least one reference sample is obtained from at least one individual not having the disease. The at least one reference sample can be available in (stored within) a database (e.g., a public database). The at least one reference sample can include a plurality of different reference samples that are available within a public database. The at least one test sample can be a sample of human cells.

Unless otherwise defined, all technical terms used herein have the same meaning as commonly understood by one of ordinary skill in the art to which this invention belongs.

As used herein, a "nucleic acid" or a "nucleic acid molecule" means a chain of two or more nucleotides such as RNA (ribonucleic acid) and DNA (deoxyribonucleic acid), and chemically-modified nucleotides. A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The terms include, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

The term "sample" is used herein in its broadest sense. A sample including polynucleotides, polypeptides, peptides, antibodies and the like may include a bodily fluid, a soluble fraction of a cell preparation or media in which cells were grown, genomic DNA, RNA or cDNA, a cell, a tissue, and the like.

By the term "reference sample" is meant a cellular population that constitutes a known comparator (a control), such as samples from healthy patients or previously characterized samples or untreated (vs. treated) samples. In a typical embodiment, when the cellular population that is under investigation (e.g. "test cells") is a population of cells from a diseased patient, one can use a population of cells from one or more subjects that are healthy as the reference sample. In some embodiments, the reference samples comprise the same type of healthy cells as the sample from the subject whose disease is predicted or assessed. The reference sample may be obtained, for example, from a normal subject, or may simply be compared to available reference values (e.g., already stored in a public database) to which the measured (test) value(s) may be compared. Typically, in a method as described herein, the test cells or plurality of test cells are the same cell type as the reference sample or samples.

As used herein, the term "replication timing domain" refers to a contiguous region of a chromosome of a cell or population of cells having a roughly the same (i.e., early vs. late) replication timing, such as a contiguous region of a chromosome of a cell or population of cells having a roughly equal replication timing ratio value.

By "replication timing profile" and "RT profile" is meant a series of values for replication timing (e.g., early versus late S-phase replication timing) along the length of at least a segment of one or more chromosome(s) within a genome. For example, the "replication timing profile" may be expressed as a series of replication timing ratio values, such as early/late S-phase replication or late/early S-phase replication, along the length of at least a segment of one or more chromosome(s), which may further be expressed on a logarithmic scale. Alternatively, the "replication timing profile" may refer to a ratio of the amounts of S-phase DNA to G1-phase DNA from a population of asynchronously dividing cells along the length of at least a segment of one or more chromosome(s), which may further be expressed on a logarithmic scale, with a higher ratio indicating earlier replication and a lower ratio indicating later replication. The term "replication timing profile" may include a replication timing fingerprint for a particular cell type or a set of replication timing fingerprints for informative segments of a replication timing profile for a particular cell type. The "replication timing profile" may be determined, for example, by quantifying an amount of replicated DNA in a sample from a population of cells by measuring fluorescently labeled DNA, by sequencing, etc. RT profiles can reveal chromosome segments with uniform replication timing, known as constant timing regions (CTRs), which often consist of several adjacent RDs that replicate within 1-2 hours.

By the terms "replication timing signature" and "RT signature" is meant a set of genome segments whose RT distinguishes a specific sample or group of samples from all others identified by unsupervised clustering analysis. For example, the genomic segments can be regions that replicate early in disease cells but late in normal cells, or vice versa.

As used herein, the term "cell type" refers to the kind, identity, and/or classification of cells according to any and all criteria, such as their tissue and species of origin, their differentiation state, whether or not (and in what manner) they are normal or diseased, etc. For example, the term "cell type" may refer separately and specifically to any specific kind of cell found in nature, such as an embryonic stem cell, a neural precursor cell, a myoblast, a mesodermal cell, etc.

For purposes of the present invention, the terms "genome-wide" or "whole genome" may refer interchangeably to the entire genome of a cell or population of cells. Alternatively, the terms "genome-wide" or "whole genome" may refer to most or nearly all of the genome. For example, the terms "genome-wide" or "whole genome" may exclude a few portions of the genome that are difficult to sequence, do not differ among cells or cell types, are not represented on a whole genome array, or raise some other issue or difficulty that prompts exclusion of such portions of the genome.

As used herein, the term "epigenetic mark" refers to a chromatin modification, e.g., proteins, post-translational modifications of proteins or RNA molecules that confer the inheritance of regulation on DNA. DNA methylation and replication timing are examples of epigenetic marks.

By the term "S/G1" is meant a method of measuring replication timing that can be used, for example, when one cannot label with BrdU or EdU because the cells in the sample have died. When this happens, a ratio of S-phase DNA to G1-phase DNA is generated, e.g., a ratio of the amounts of S-phase DNA to G1-phase DNA from a population of asynchronously dividing cells along the length of at least a segment of one or more chromosome(s), which may further be expressed on a logarithmic scale, with a higher ratio indicating earlier replication and a lower ratio indicating later replication.

As used herein, the term "E/L" means a method of measuring replication timing typically used when one can metabolically label with BrdU or EdU. For example, a replication timing profile may be expressed as a series of replication timing ratio values, such as early/late S-phase replication, along the length of at least a segment of one or more chromosome(s), which may further be expressed on a logarithmic scale.

The phrases "isolated" or "biologically pure" refer to material which is substantially or essentially free from components that normally accompany it as found in its native state.

The terms "patient" "subject" and "individual" are used interchangeably herein, and mean an animal from which a sample is obtained, including vertebrates and invertebrates. Typically, a subject is a human. In some cases, the methods of the invention find use in experimental animals, in veterinary applications (e.g., equine, bovine, ovine, canine, feline, avian, etc.), and in the development of animal models for disease, including, but not limited to, rodents including mice, rats, and hamsters, as well as non-human primates.

Although methods similar or equivalent to those described herein can be used in the practice or testing of the present invention, suitable methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1A: Genome-wide profiling of RT protocol. FIG. 1B: Schematic diagram showing the three germ layers and the neural crest during the early stages of human development and differentiation pathways of the distinct cell types analyzed. Solid arrow lines depict the in vitro differentiation pathways of the distinct cell types from hESCs; dashed arrows depict the embryonic origin of the cell types not derived from hESCs (primary cells and cell lines). FIG. 1C: RT changes across the different lineages. The whole genome was divided into 13,305 windows of 200 kb and their average RT ratios [=$\log_2$(Early/Late)] were compared across the human lineages. Heat map shows the RT ratios. FIG. 1D: Hierarchical clustering of the distinct human lineages and k-means of switching 200-kb windows. Switching 200-kb segments were identified as being early replicated in at least one cell type (RT $\log_2$ ratio≥+0.3) and late replicated in at least one other cell type (RT $\log_2$ ratio≤−0.3) and analyzed by hierarchical clustering of the cell types. Branches of the dendrogram were constructed based on the correlation values between distinct cell types (distance=correlation value−1). A correlation threshold of >0.5 was used to color label the major groups of cell types. Specific clusters of cell types are indicated at the bottom: pluripotent, definitive endoderm, liver and pancreas, neural crest and early mesoderm, late mesoderm and fibroblasts, NPC, myeloid, and lymphoid. k-means clustering of switching segments defined the RT signatures labeled in gray boxes. The sex chromosomes were removed from the analysis to discard gender differences. (NC) neural crest; (MED) mesendoderm; (DE) definitive endoderm; (LPM) lateral plate mesoderm; (Splanc) splanchnic mesoderm; (Mesothel) mesothelium; (SM) smooth muscle; (Myob) myoblasts; (Fibrob) fibroblasts; (MSC) mesenchymal stem cells; (NPC) neural progenitor cells.

FIG. 2A, 2B, 2C: RT switching segments have a distinct sequence composition.

FIG. 2A: Characterization of a genomic region from Chromosome 6. Top panels display the gene density, GC content, and densities of interspersed repetitive sequences (LINEs and SINEs). Below are the RT profiles of the same genomic region in distinct cell types. Bars in each plot highlight segments of the Chromosome 6 replicating differentially in specific cell types. FIG. 2(B) Density contours were plotted for gene density, GC content, and densities of LINEs and SINEs. Correlations of distinct genomic features were calculated against RT from hESC and hepatocytes. The top and right side histograms depict the density distribution of each feature.

FIG. 2C: Box plots of gene density, GC content, densities of LINEs and SINEs, and GC content of constitutive (Early and Late) and switching 200-kb regions: (***) P<0.001.

FIG. 3A, 3B, 3C, 3D: Replication domain (RD) reorganization during hESC differentiation. FIG. 3A: Number and sizes of constant timing regions (CTRs) in the distinct pathways. Solid lines depict the average size of the CTRs, whereas dashed lines depict the total number of CTRs in each cell type. FIG. 3B: Sizes of early and late replicating CTRs during differentiation toward pancreas, mesothelium, and smooth muscle: (**) P<0.01 compared to hESC. FIG. 3C: Representative RD consolidation during hESC differentiation. FIG. 3D: Deconsolidation of RD during MSC differentiation.

FIG. 4A, 4B, 4C, 4D, 4E, 4F, 4G, 4H: Dynamic changes in RT and transcriptional activity during hESC differentiation. FIG. 4A: Frequency distributions of 200-kb segments and RefSeq genes in early and late S-phase fractions. The first row includes a pool of 200-kb or RefSeq genes (All) across all cell types; the second row includes only the RT-constitutive regions (i.e., does change RT in any cell type); and the third row includes only the regions or genes switching RT at least in one cell type. RT changes during hESC differentiation toward endoderm FIG. 4B: mesoderm FIG. 4C: and ectoderm FIG. 4D: Averaged RT values at the TSS of 27,544 RefSeq genes were obtained; the switching genes were extracted according to the same criteria of FIGS. 1A-1D and analyzed by hierarchical clustering and k-means. The heat map shows the RT ratios [=$\log_2$(Early/Late)]. Branches of the dendrogram were constructed based on the correlation values (distance=correlation value−1), and distinct correlation thresholds were used to color label the major nodes. The sex chromosomes were removed from the analysis to discard gender differences. The k-means clusters are shown as numbered gray boxes. FIG. 4E, 4F, 4G, 4H: Transcriptional regulation and its relationship with RT dynamics for RT-constitutive genes FIG. 4E, genes switching EtoL and LtoE FIG. 4F, EtoLtoE FIG. 4G, and LtoEtoL FIG. 4H. Note that in FIG. 4E, some genes appear to switch RT but do not meet the RT-switching cutoff used in this study. FIG. 4F, 4G, 4H: Genes with a fold difference ≥6 in expression level compared with hESC at any differentiation stage were classified into the RT clusters from panels FIG. 4B to FIG. 4D to identify the kinetics of regulation. Line graphs depict the dynamics in RT of each cluster, and box plots were used to display the transcriptional ratios against expression in hESC: (*) P≤0.05; () P≤0.01; (*) P<0.001 compared to hESC.

FIG. 5A: Correlation between early replication and the probability of expression changes during differentiation. Genes were scored as either expressed or not expressed and ranked by their RT ratio and divided into bins of 100 genes, the height of which represents the percentage of expressed genes within each bin. Logistic regression (inner line) and 95% confidence intervals (outer lines) reveal the correlation strength. Top row graphs include all genes, the middle includes only the RT-constitutive genes (i.e., do not change RT), and the bottom row includes only the genes that change RT during differentiation from hESC to pancreatic endoderm. FIG. 5B: Distinct classes of switching genes. Transcriptional activity (top graphs) and RT (bottom graphs) of exemplary genes representing the distinct kind of switching classes: E-class genes are only expressed when early replicating (ALB); L-class genes can be expressed only when late replicating (CUBN); C-class genes can be transcribed whether early or late replicating (LYN); and N-class are genes with no transcriptional activity detected in the cell types profiled (FOXL1).

FIG. 5C: Frequencies of the distinct kind of genes based on their RT dynamics during differentiation. RT-constitutive genes were classified as O-class. FIG. 5D: Density plots of all RefSeq genes, RT-constitutive and RT-switching genes, and the distinct categories of RT-switching genes according to their RT and transcriptional level.

FIG. 6A, 6B, 6C, 6D, 6E, 6F, 6G, 6H, 6I, 6J: Gene expression regulation and RT changes. FIG. 6A: RT changes were collected from all transition stages in all differentiation pathways, and the percentages of expressed genes in each stage (before and after the RT switch) were obtained. The first columns in EtoL and LtoE changes contain the percentages of genes expressed calculated from the total number of switching genes in each category. The last columns contain the percentages of genes expressed before/after the RT switch. EtoL changes=3567 genes, and LtoE changes=3098 genes. FIG. 6B: Expression levels of the distinct classes of RT-switch-ing genes during the EtoL (upper) and LtoE (lower) RT changes. FIG. 6C: Expression levels of the distinct classes of RT-switching genes during the EtoMtoL (upper) and LtoMtoE (lower) RT changes. Transcriptional values were obtained from all respective RT changes occurring in between all intermediate stages of all differentiation pathways. FIG. 6D-6F illustrate the transcriptional regulation and RT dynamic changes in endoderm (FIG. 6D), mesoderm (FIG. 6E), and ectoderm (FIG. 6F) differentiation per RT switching class. The genes with a fold difference ≥6 compared with hESC were classified into the RT clusters from FIGS. 4B-4D and separated in the distinct categories of RT-switching genes to identify the kinetics of regulation. Line graphs depict the dynamics in RT of each cluster, and box plots were used to display the transcriptional levels across the differentiation pathways: (*) P≤0.05; () P≤0.01; (*) P<0.001 compared to hESC. Specific stages of differentiation are shown at the bottom. FIG. 6G: Densities of regulatory interactions among E-class, C-class, and O-class genes. The probability of inter-class regulation was calculated by defining each class of genes by different values of RT cutoff (RTC), stringency (PCT), and switch cutoff (SC). Each PCT row is a composite of six rows representing SC values of 0.5 to 1.0 from the bottom up. Each cell represents the probability of the x-axis gene class regulating the y-axis gene class, based on the corresponding values of RTC, PCT, and SC. H-I Switching genes are preferentially located at the TTRs. Densities of the TSS from the distinct categories of genes were calculated as a function of their distance to the early replication boundary and plotted according to their RT (FIG. 6H) or probability densities (FIG. 6I). FIG. 6J: Induction of C-class genes precedes EtoL RT changes and induction of E-class genes. Expression levels (top graphs) and RT changes (bottom graphs) of representative genomic regions during differentiation.

FIG. 8A: Graphical depiction of the RT and switching cutoffs. The "RT cutoff" (RTC) defines the point of log 2 ratio at which the changes are determined, "switching cutoff" (SC) refers to the size of the change and is depicted as the maximum and minimum vertical lines. FIG. 8B: Frequency of RT-switching 200 kb segments using distinct RT and switching cutoffs and the RT signatures identified using distinct exemplary combinations of cutoffs. Distinct combinations of cutoffs were tested to select the parameters that best distinguished cell types (RT signature identification).

FIG. 11A, 11B, 11C, 11D, 11E: Replication timing abnormalities in HGPS. FIG. 11A: Schematic depiction of the distinct cell samples analyzed by genome-wide RT profiling. Primary fibroblasts derived from HGPS patients, and healthy fetal (IMR90), neonatal (BJ), young (10 and 11 yr), adult (30 yr) and aged donors (74-96 yr) were pulse labeled with BrdU, sorted into early and late S-phase fractions and RT programs were obtained either by array hybridization or NGS. FIG. 11B and FIG. 11C: Representative immunofluorescence staining of primary fibroblasts from healthy FIG. 11B or HGPS patients FIG. 11C. Images show DNA staining (DAPI) and immunodetection of Lamin-B and γH2AX. FIG. 11D: Correlation matrix of genome-wide RT programs of HGPS fibroblasts and cells from distinct healthy donors across a wide range of ages representing natural aging and cellular senescence (PreS=cellular senescence induced by serial passaging, OIS=oncogene induced senescence). FIG. 11E: RT profiles of exemplary chromosome segments showing RT alterations in progeria. The RT profiles are displayed as log 2 ratios of signals from early and late S-phase fractions, positive values correspond to early replication while negative values correspond to genomic regions that replicated late during S-phase. RT alterations in HGPS are highlighted by dashed boxes.

FIG. 12A: RT differences between HGPS and normal fibroblasts. Very small differences in the RT program are observed between normal fibroblasts (top panel) while HGPS showed increased differences when comparing to normal cells derived from donors of similar age. RT variable regions were identified as those that display differences ≥1 in pairwise comparisons between all samples analyzed. FIG. 12B A progeria-specific RT signature distinguishes HGPS fibroblasts from normal cells. Unsupervised clustering analysis of RT variable chromosomal segments identified specific RT signatures. Heat map shows the RT ratios [=log 2(Early/Late)]. Branches of the dendrogram were constructed based on the correlation values (distance=correlation value−1) and a correlation threshold of 0.6 was used to define three main sample clusters: fetal, postnatal normal and HGPS. k-means analysis of variable segments defined RT signatures (set of chromosomal domains that replicate abnormally during S-phase). FIG. 12C: RT values of genomic regions from the 'E-progeria' RT signature. Significant differences based on pairwise T-test with bonferroni adjustment are shown (p-value<1×10$^{-5}$, *p-value<2×10$^{-16}$). FIG. 12D and FIG. 12E: RT profiles of exemplary genomic regions from the progeria-specific RT signature FIG. 12D and additional RT signatures FIG. 12E. Dashed boxes highlight significant changes. FIG. 12F Ontology analysis revealed that RT abnormalities in progeria are strongly associated with the phenotypic characteristics of HGPS disease. Analysis was performed with the GREAT Tool (McLean et al., 2010). Statistical significance measured by binomial test.

FIG. 13A: TP63 gene is a potential driver of the HGPS phenotype. Overlap analysis of the genes within each ontology term associated with the progeria-specific RT signature (see FIG. 12F) reveals TP63 as unique gene linked with the phenotypic characteristics of HGPS. Additional ontology terms annotated for the regions within the progeria-specific RT signature and linked to TP63 abnormalities are shown in the table at the right. FIG. 13B and FIG. 13C: The TP63 locus replicates early in progeria cells but late in all fibroblasts derived from healthy donors of distinct ages as well as in cells entering senescence. FIG. 13D: Loss of H3K27me3 peaks at the TP63 gene in HGPS fibroblasts. H3K27me3 from a HGPS patient and a healthy donor of similar age are shown. Chromosome position of TP63 is highlighted.

FIG. 14A: Schematic representation of reprogramming to iPSCs and re-differentiation back to fibroblasts of primary cells as a model of HGPS disease progression. FIG. 14B: Reprogramming to iPSCs reverts the nuclear abnormalities characteristic of HGPS disease which are spontaneously reestablished upon differentiation to fibroblasts. Representative immunofluorescence images of normal and HGPS: DNA (DAPI), Lamin B and γH2AX. FIG. 14C: Correlation matrix of genome-wide RT program from normal, HGPS and RTS fibroblasts, the corresponding reprogrammed iPSCs and re-differentiated cells. Cells derived from patients with progeroid diseases (HGPS and RTS) are highlighted in bold letters. The cell types are specified at the bottom (primary fibroblasts, reprogrammed iPSCs and re-differentiated cells). The source of the samples is shown at the right: HGPS, RTS and control samples from fetal, newborn, young and aging. FIG. 14D: Clustering analysis of all fibroblasts samples as in FIG. 12A, 12B, 12C, 12D, 12E, 12F including the re-differentiated cells from iPSCs derived from healthy donors, and HGPS and RTS patients. Heat map shows the RT ratios [=log 2(Early/Late)]. Branches of the dendrogram were constructed based on the correlation values (distance=correlation value−1) and a correlation threshold of 0.4 was used to define main sample clusters. Only regions from the 'E-progeria' RT signature are shown. FIG. 14E and FIG. 14F: Altered RT of TP63 is reestablished in re-differentiated cells from HGPS and RTS even before other nuclear abnormalities are observed. HGPS and RTS cells were reprogrammed to iPSCs and re-differentiated back to fibroblasts. RT of primary cells, iPSCs and early passages (p4) of re-differentiated cells are shown. RT of fibroblasts from a healthy donor is shown as a control. Chromosome position of TP63 is highlighted.

FIG. 15A: Schematic depiction of TP63 locus organization and gene regulation between normal and progeroid fibroblasts. In normal cells, TP63 is localized to late replication compartments where it is lowly expressed (consistent with an increased enrichment of H3K27me3). In contrast, in cells from patients with progeroid diseases, the TP63 gene replicates early and is depleted of H3K27me3, which is associated with unbalanced isoform expression. FIG. 15B: Altered isoform expression of TP63 is associated with distinct defects of ectodermal development and epidermis regulation.

FIG. 16A: 66 patient samples (fresh and frozen banked BM or PB and 1 cell line) were subjected to RT profiling. The genome was divided in 63,522 50 kb segments ("RT features"), 3,577 of which varied (above cut-off) in RT. The RT values of each variant RT feature were subjected to unsupervised K-means clustering (K=9), revealing distinctive "RT signatures". TCF3-PBX1 is highlighted to illustrate the common (#1 and #2) and divergent (#3) RT signatures within this BCP-ALL subtype. FIG. 16B: Hierarchical clustering of all patients along with non-leukemic cell types profiled to date, using the RT features within Signature #1. Several NOS patients share many features of this signature. FIG. 16C: Clustering as in B but using a subset of 40 RT features from RT Signature #1 that replicate early in pre-B cells but not pro-B cells. FIG. 16D: RT plots for one of the RT features in FIG. 16C that contains the ROR1 tyrosine receptor kinase gene for TCF3-PBX1 patients relative to all other BCP-ALL patients (Top) or relative to other non-leukemic cell types (Bottom). Myeloid cells are MPB=G–CSF mobilized peripheral blood; CD34=purified MPB CD34+ cells; MyeD3,D5/EpoD3/D5/TPOD6=CD34+ cells differentiated into myeloid (granulocytes-macrophages)/erythroid/megakaryocytes for 3 or 5 days. Lymphoid cells are 8 EBV-immortalized non-malignant cell lines, adult CD4+ peripheral T-cells and CD34+CD19+ (pro-B) and CD34-CD19+ (pre-B)-cells regenerated from CD34+ CB cells in immune-deficient mice. Patient samples are labeled by their unique COG or OHSU identifiers and, where cytogenetics are known, are categorized into BCR-ABL, TEL1-AML1, TCF3-PBX1 or NOS BCP-ALL subtypes.

DETAILED DESCRIPTION

Described herein are novel methods for identifying and classifying differences between biological samples based on RT data. By comparing RT data for a test sample(s) to RT data for already characterized samples, one can identify differences and profile any new cell type or disease. These new methods allow for the detection of all the changes between distinct samples, many of which would escape detection by previous methods that discard any features showing any intra-sample variation. In some embodiments, these RT methods are used to identify disease-specific abnormalities not detected by other methods. For example, the experiments described herein demonstrate the power of RT signatures to distinguish progeroid syndromes from normal aging and cellular senescence. By comparing cells from Hutchinson-Gilford Progeria (HGPS) and Rothmund-Thomson (RTS) syndrome patients to cells from healthy donors of distinct ages (fetal to 96 yrs), a progeroid-specific RT signature (set of chromosomal domains that replicate abnormally during S-phase) was identified. By reprogramming patient cells to iPSCs followed by re-differentiation as a model of disease progression, the earliest RT abnormalities to appear were tracked. The TP63 gene was identified as one of the earliest RT abnormalities to appear during iPSCs differentiation. Although TP63 has been implicated in other aging-related diseases, no previous molecular alterations in this gene have been found in progeroid syndrome patients. In fact, what was found is that while TP63 is expressed at similar levels in progeroid and normal cells, differential usage of alternative promoters produces a significant preference for one of two major TP63 isoforms. Altogether, these findings take a novel approach (RT signatures) for disease marker discovery and identified a common gene alteration associated with the pathophysiological manifestations of progeroid diseases.

The below described preferred embodiments illustrate adaptations of these methods. Nonetheless, from the description of these embodiments, other aspects of the invention can be made and/or practiced based on the description provided below.

Methods of Identifying a RT Signature(s) and Uses Thereof

Figure 1A:
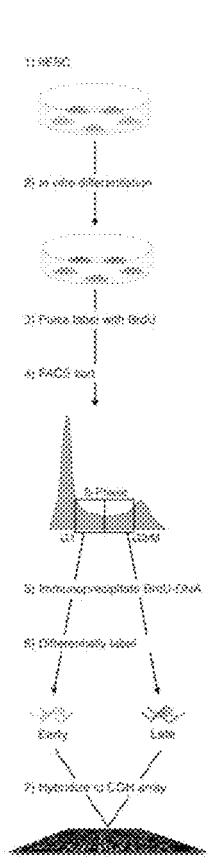
FIG. 1A, 1B, 1C, 1D: Genome-wide RT patterns are lineage specific.
Figure 1B:
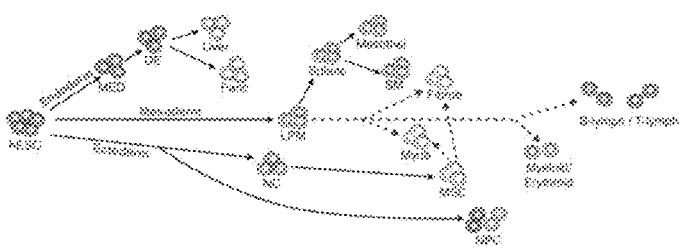
Figures 1C, 1D:
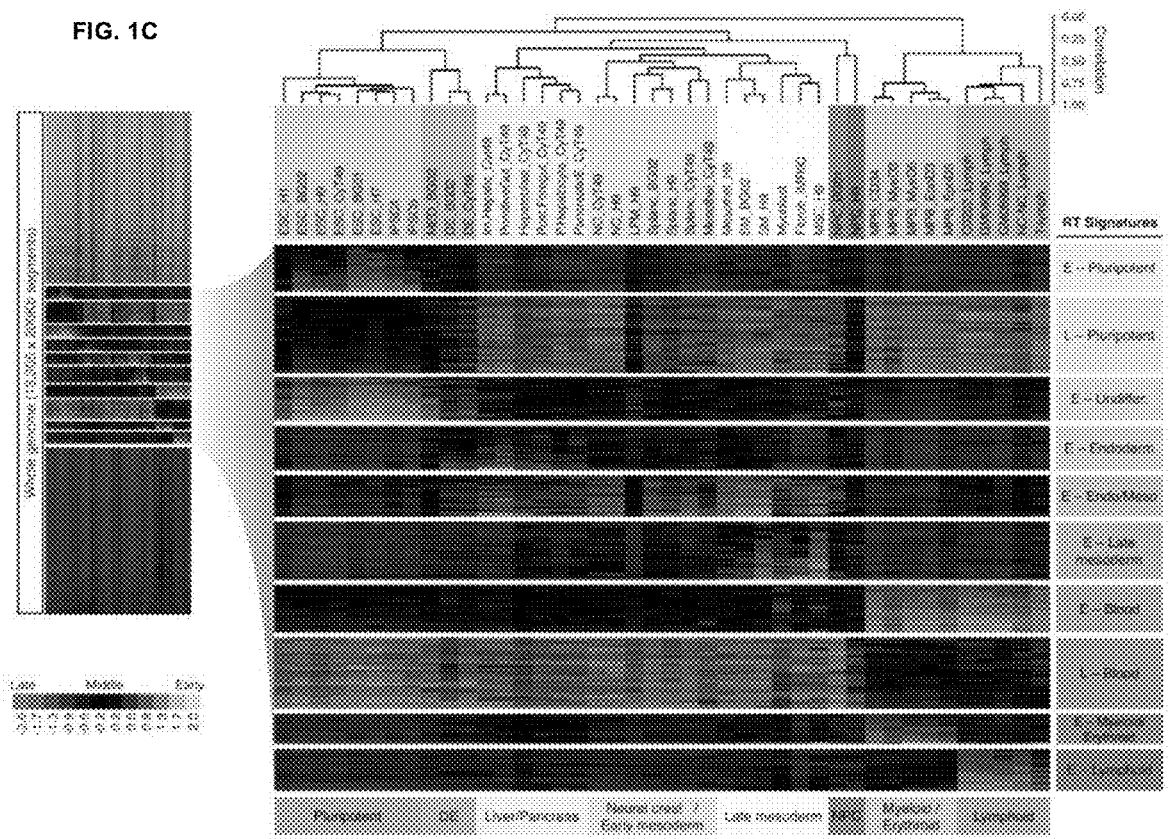

Generating a RT signature typically involves the identification of specific replication features of multiple groups of samples at once. The advantage of RT signatures identification is the ability to detect and classify all the differences between as many samples as one likes all at once. An example of a RT signature is shown in FIG. 1(D). RT signature identification is processed in an unsupervised way (i.e. no pre-defined groups), so that any difference between any groups samples can be identified and classified without defining the set of samples a priori, facilitating the discovery of novel features of RT that are sample-specific, as well as discovering groups rather than looking for the top differences between known groups. Since the identification of RT signatures captures all the variability of the samples, all of the features can be classified into sample-specific RT signatures.

A typical method of identifying a RT signature for a test sample of cells (e.g., human cells) or plurality of test samples of cells includes the following steps: generating a RT profile for the test sample or RT profiles for the plurality of test samples; generating a RT profile for at least one reference sample; removing pericentromeric and subtelomeric regions to remove large repetitive DNA regions from the test sample and reference sample RT profiles; dividing genomes or sub-genomic regions into about 50 to about 200 (e.g., 40, 45, 49, 50, 55, 60, 65, 70, 75, 80, 85, 90, 95, 100, 110, 125, 150, 175, 180, 185, 190, 199, 200, 201, 205, etc.) kb non-overlapping windows and averaging the RT values within each window; removing chromosome segments having invariant RT between test and reference samples resulting in a collection of remaining chromosome segments that include all variation in RT between the samples such that the remaining chromosome segments are variant regions; performing k-means clustering of the variant regions to identify specific patterns of RT and hierarchical clustering of all samples; when all samples are processed, defining a threshold in correlation values of the hierarchical clustering to identify groups of samples that are related by their RT; and identifying RT signatures that distinguish the test sample or plurality of test samples from the reference sample that is the set of chromosome segments whose RT best distinguishes the test sample or plurality of test samples. In some embodiments, in addition to pericentromeric and subtelomeric regions, sex chromosomes are removed to discard gender differences.

Typically, the test sample of cells (e.g., human cells) or plurality of test samples of cells is not pre-defined, allowing discovery of novel subsets of samples distinguished by specific RT signatures. The at least one reference sample can be stored within a database. In some embodiments, a RT signature for a test sample is compared to a plurality (e.g., 5, 10, 100, 1000, etc.) of reference samples in a database. In some embodiments, RT profiles for both the reference sample(s) and the test sample(s) are generated, while in other embodiments, an RT profile for a test sample(s) can be generated and compared to a large pre-existing collection (e.g., a database) of RT profiles (e.g., RT profiles of reference samples, reference RT profiles). One such example of an RT profile database is that of replicationdomain.com. When referring to a test sample or starting sample, the sample can contain any type of cells that are proliferating, so that replication timing can be measured. Because one can measure RT and identify RT signatures of any proliferating cells, the choice of test or starting sample(s) (e.g., the choice of cell type(s)) depends on the particular analysis being undertaken (i.e., the analysis of interest, in some instances, one that is dependent on the available samples). For example, in the experiments described herein, multiple cell types derived from human stem cells were analyzed and lineage-specific RT signatures were found. As another example, also in the experiments described herein, the question was asked whether or not RT is altered in Hutchinson-Gilford progeria syndrome. To address this question, samples from patients and healthy donors were analyzed and progeria-specific RT signatures were identified. Similarly, the methods described herein can be used to analyze samples of any disease, compare them with a normal (disease-free) control, and if RT is altered in the disease, identify disease-specific RT signatures. A plurality of samples (e.g., test samples) to be analyzed can contain different cell types (e.g., a first sample contains cell type A, a second sample contains cell type B, a third sample contains cell type C, etc.). In other embodiments, a plurality of samples to be analyzed can contain the same cell type, but a subset of the plurality of samples can contain cells from a diseased subject, while a subset or the remainder of samples can contain cells from a non-diseased (e.g., normal) subject.

A first or early step in a typical method is generating a RT profile for one or more test samples, and in some embodiments, a RT profile for one or more reference samples. Generating a RT profile can be done by any suitable method(s), e.g., array hybridization and/or sequencing, S/G1, E/L, etc. Methods for generating and analyzing RT profiles are known in the art and are described, for example, in U.S. Pat. Nos. 9,245,090, 8,725,423, and 8,728,979, and Ryba et al. 2011 Nat Protoc. 6(6): 870-895. These references are incorporated herein by reference in their entireties.

In the method, a RT signature specific for the test sample of cells or plurality of test samples of cells can identify a set of chromosome regions whose RT can distinguish the test sample of cells or plurality of test samples of cells. RT signatures are the specific k-means clusters of chromosome segments that replicate differently between reference and test sample(s). The specific k-means clusters are those that replicate either earlier or later in the test samples or plurality of test samples as compared with the at least one reference sample. Clustering approaches, including k-means clustering and hierarchical clustering, are known in the art. See, for example, U.S. Pat. No. 8,725,423, and Ryba et al. 2011 Nat Protoc. 6(6):870-895, both of which are incorporated herein by reference in their entireties.

Typically, when referring to a "group of samples" or "groups of samples," a group includes samples sharing high correlation values (e.g. that are identified within the same branch of a dendrogram after hierarchical clustering analysis of the samples). A group can include any suitable number of samples. The number of samples is typically dependent upon how similar or heterogeneous the samples are because group identification is based on the correlation values between the samples. For example, in the experiments described in Example 1 below, many clusters were found because there was a broad collection of distinct cell types.

In the experiments described herein, the whole genome except for the sex chromosomes and repetitive DNA was analyzed for generating genome-wide data. However, the methods described herein can be performed at any (e.g., one or more) specific subset(s) of the genome, including sex chromosomes when appropriate. For example, RT profiles can be generated for genomes, or for sub-genomic regions. When referring to "parameters" herein, the parameters are generally only the thresholds to extract variant regions, and these variant regions can then be classified by an appropriate clustering algorithm in the distinct RT signatures.

The methods described herein can be used to generate a RT signature for a particular cell type as well as for generating a plurality of RT signatures for a plurality of samples (e.g., having different cell types) given that there is sufficient variability in RT to distinguish them. In an embodiment in which one has a set of samples and wishes to identify the cell type(s) present in that sample, the method typically includes 1) the extraction of RT variant regions and their classification by unsupervised k-means clustering to identify the RT signatures specific for the samples analyzed and 2) the hierarchical clustering of the samples along with samples of known cell types to identify to which cell type each sample belongs.

Once sample-specific RT signatures are obtained, characterization of sample-specific RT signatures can be performed by ontology analysis comparing the set of regions in each RT signature against the genome. This allows one to identify specific features within the RT signatures that might be already associated with the specific group of samples distinguished by their RT. Such an ontology analysis can be used to interpret RT signatures and to find out whether specific features within each RT signature have been already associated or not to the group of samples. Such an analysis can be used to identify a novel biomarker and/or therapeutic target of a particular disease. The RT signature of the test sample of cells or plurality of test samples of cells can be used, for example, to identify a particular disease. For example, a method of identifying a disease-specific RT signature can include generating at least one RT signature specific for at least one test sample of diseased cells as compared to at least one non-diseased reference sample according to the method described above for identifying a RT signature for a test sample of cells.

As another example, a method of identifying a novel marker of a disease can include the method above for identifying a RT signature for a sample of cells resulting in at least one sample-specific RT signature for at least one test sample that contains disease-specific cells, and identifying and characterizing key features of the sample-specific RT signature. In this method, identifying and characterizing key features can be done, for example, by ontology analysis to determine whether chromosome regions within the sample-specific RT signature have been annotated with terms relevant for the at least one test sample. As another example, identifying and characterizing key features can be done by comparing RT against other genomics data to determine the relevance of the sample-specific RT signature for at least one test sample. Other genomics data can include, for example, gene expression, epigenetic marks, and regulatory elements. In this method, a potential novel marker and/or a therapeutic target for the at least one test (disease) sample can be identified within the features of the sample-specific RT signature after the ontology analysis and comparison against other genomics data, as those chromosome segments with abnormal RT that might be associated with de-regulation of specific genes linked to the disease.

In the Examples below, cells were labeled with the nucleoside BrdU (bromodeoxyuridine). In other experiments, BrdU was compared to 5-ethynyl-2'-deoxyuridine (EdU) and it was found that EdU was more sensitive. Thus, EdU and any other suitable modified nucleosides may also be used in the methods and assays described herein, such as, for example, iododeoxyuridine (IdU), and chlorodeoxyuridine (CldU).

Methods of RT Profiling Applicable to Primary Human Acute Lymphoid Leukemias (ALL) without Nucleoside Labeling A major challenge to interrogating some genetic issues in human acute lymphoid leukemia (ALL) is the low proliferative activity of most of the cells, which may be further reduced in cryopreserved samples and difficult to overcome in vitro. In contrast, the ability of many human ALL cell populations to expand when transplanted in highly immunodeficient mice is well documented. To examine the stability of DNA RT profiles of serially passaged xenografts of primary human B- and T-ALL cells, a method was devised that circumvents the need for nucleoside labeling to distinguish early versus late S-phase cells. Using this and more standard protocols, consistent strong retention was found in xenografts of the original patient-specific RT features, for all 8 primary human ALL cases surveyed (7 B-ALLs and one T-ALL). Moreover, in a case where genomic analyses indicated changing subclonal dynamics in serial passages, the RT profiles tracked concordantly. These results show that DNA RT is a relatively stable feature of human ALLs propagated in immunodeficient mice. In addition, they suggest the power of this approach for future interrogation of the origin and consequences of altered DNA RT in these diseases. The experiments described below in Example 3 demonstrate the establishment of genome-wide DNA RT profiling methodology applicable to primary human ALLs without BrdU labeling, and that RT is a relatively stable characteristic of individual patients' ALL cells. Accordingly, in the methods described herein, the cells (e.g., the test sample of cells or plurality of test samples of cells) can be frozen banked cells that have been cultured and expanded in patient-derived xenografted mice.

EXAMPLES

The present invention is further illustrated by the following specific examples. The examples are provided for illustration only and should not be construed as limiting the scope of the invention in any way.

Example 1

Dynamic Changes in Replication Timing and Gene Expression During Lineage Specification of Human Pluripotent Stem Cells Early replication is globally associated with active gene expression in all multicellular organisms, and developmentally regulated changes in RT are generally coordinated with transcriptional competence. However, causal relationships between RT and gene expression remain a long-standing puzzle. Previous studies during early mouse development found coordinated changes in transcription and RT, but could not distinguish which changes first. Recently developed methods for human embryonic stem cell (hESC) differentiation allow a highly synchronous derivation of distinct lineages and provide a unique opportunity to study the mechanisms that regulate the establishment of cell-type-specific RT programs and its relationship to differential gene expression, pluripotency, and lineage specification.

Herein, genome-wide RT and transcriptome data from 26 distinct human cell types representing each of the three embryonic germ layers and neural crest including several key intermediate stages were generated. This study constitutes the most comprehensive characterization of dynamic changes in the temporal order of replication and gene expression during human development and identifies lineage-specific RT programs and genes that change RT during distinct lineage differentiation pathways. In contradiction to all prior literature, two-thirds of genes that switched RT were transcriptionally active and late replicating in at least one cell type. Moreover, these genes were significantly more central in transcriptional regulatory networks than the smaller class of genes that were only expressed when early replicating. Taken together, these results support a hierarchical model that links global chromatin organization and RT control with gene regulatory networks during human development.

Results

Genome-Wide RT Programs of Human Cell Types

Figure 8A:
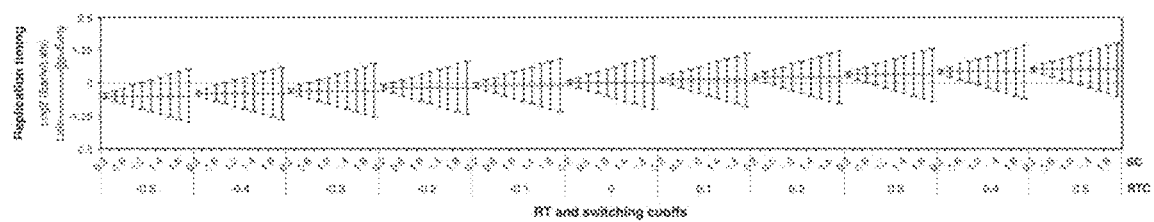
FIG. 8A, 8B: RT and switching cutoffs used to identify the RT-switching regions (200 kb segments).
Figure 8B:
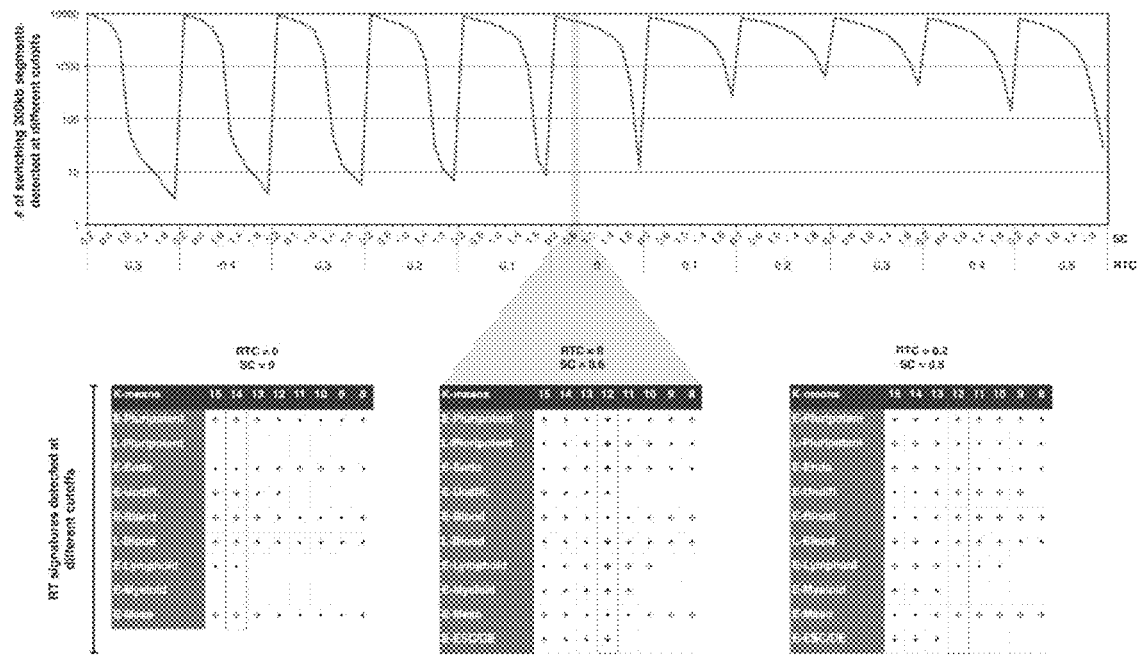

Genome-wide RT profiles were obtained as previously described (Hiratani et al. PLoS Biol 6: e245 (2008); Ryba et al. Nat Protoc 6: 870-895 (2011)). Briefly, cells were labeled with BrdU, retroactively synchronized into early and late S-phase fractions by flow cytometry, and BrdU-substituted DNA from early and late S-phase populations was immunoprecipitated, differentially labeled, and cohybridized to a whole-genome oligo-nucleotide microarray (FIG. 1A). To compare all 84 data sets representing 26 distinct cell types, RT profiles were expressed as numeric vectors of 13,305 average RT ratios for nonoverlapping 200-kb windows across the genome, excluding sex chromosomes and long stretches of repetitive DNA. Correlation analysis confirmed close correspondence of technical and biological replicates (independently differentiated from hESC), which were averaged for subsequent analysis. Distinct combinations of thresholds were tested for defining genomic segments that change RT during development ("switching RT regions") and chose parameters that best distinguished cell types by RT (FIG. 8). Switching regions were defined as being $\geq+0.3$ (Early) in at least one cell type and $\leq-0.3$ in at least one cell type. Using these criteria, which are relatively stringent compared to prior cut-offs (Hansen et al. Proc Natl Acad Sci 107: 139-144 (2010); Hiratani et al. Genome Res 20: 155-169 (2010); Farkash-Amar et al. PLoS One 7: e48986 (2012)), 30.5% of the genome was selected as changing RT during differentiation.

To analyze developmental transitions in RT, genome segments that were invariant between cell types ("RT-constitutive regions") were removed and hierarchical and k-means clustering analysis of the switching segments (FIG. 1C,D) were performed. As expected, cell types clustered according to their developmental lineages (FIG. 1B,D). Importantly, normal primary cells extracted from healthy donors (myoblasts, T-lymphocytes), cell types differentiated in vitro from primary cells (hESCs and mobilized peripheral blood), and cell lines (fibroblasts IMR90 and EBV immortalized B-lymphocytes) clustered with their related cell types according to their developmental origin rather than their derivation history (FIG. 1D). Interestingly, both neural crest (NC), a uniquely vertebrate tissue derived from ectoderm, and NC-derived mesenchymal stem cells (MSC), which can be differentiated into cell types typically derived from mesoderm, clustered with mesoderm cell types, suggesting a close alignment of chromosome architecture in NC with mesoderm tissues (FIG. 1D). Also, the RT program of blood cells was substantially different from other cell types, with lymphoid and myeloid/erythroid lineages forming distinct subclusters (FIG. 1D).

RT Signatures Distinguish the Major Human Lineages k-means clustering of RT switching regions identified specific clusters of 200-kb windows replicating at times unique to specific lineages, which are referred to herein as RT signatures (FIG. 1D). Features of these signatures are highlighted below.

An RT signature for pluripotency

Figure 9:
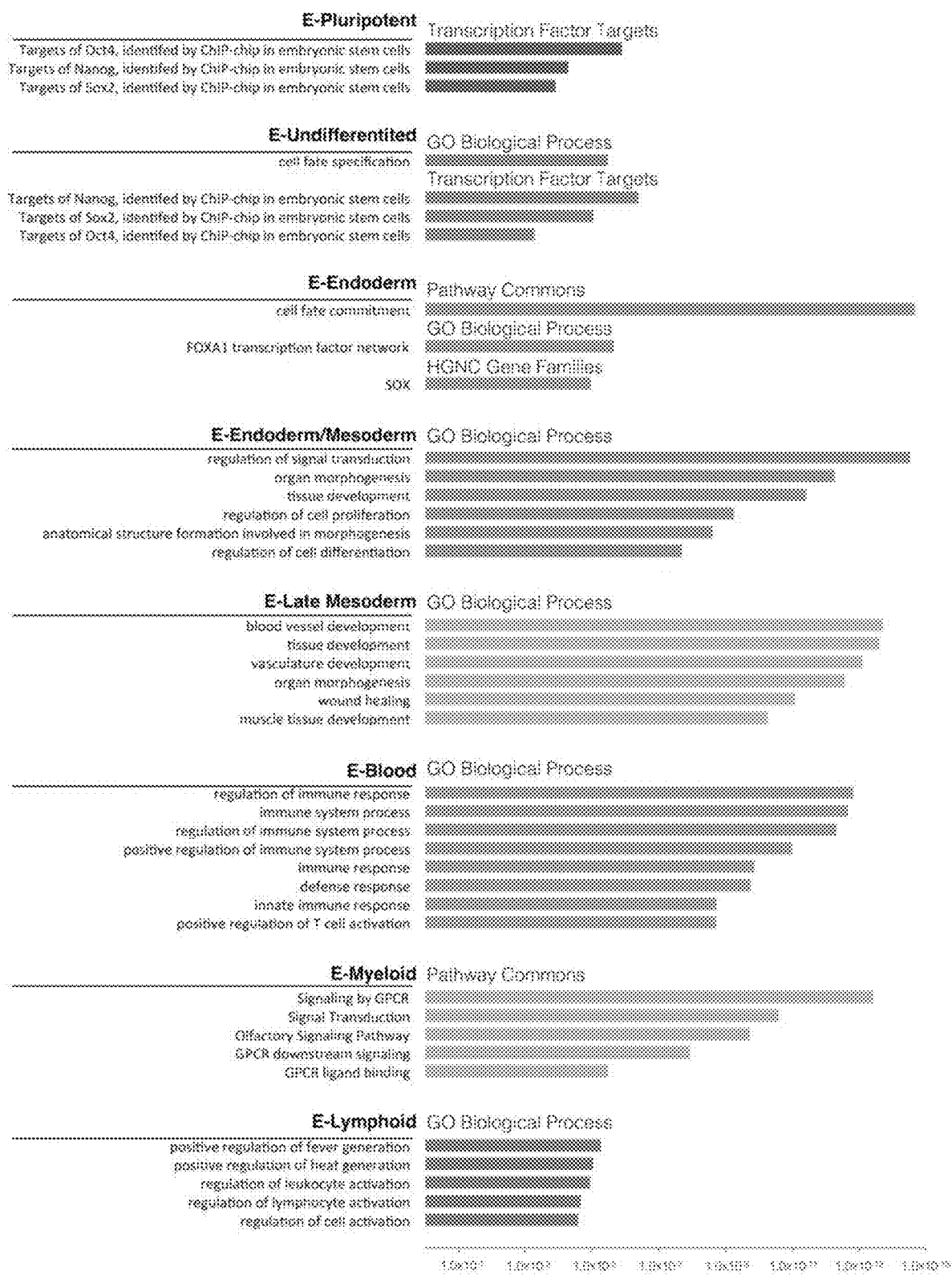
FIG. 9: Ontology analysis of the distinct RT signatures. Analysis was performed with the Genomic Regions Enrichment of Annotations Tool (GREAT)(McLean et al. 2010) using the distinct RT signatures of 200 kb segments obtained by K-means clustering. At the bottom is shown the statistical significance (p-values measured by binomial test).

Regions from the E-Pluripotent RT signature were replicated early in hES and iPS cells and late in all differentiated cell types (FIG. 1D). These segments included genes known to be involved in maintaining pluripotency such as DPPA2, DPPA4, and ZFP42 and were significantly enriched for genes whose promoters contain binding sequences for pluripotency transcription factors POU5F1, NANOG, and SOX2 (FIG. 9). An RT signature (E-Undifferentiated) of regions uniquely early replicating in hESC and early stages of endoderm and mesoderm (FIG. 1D) were identified; these segments were enriched for genes involved in cell fate specification as well as genes with target sequences for NANOG, SOX2, and POU5F1 (FIG. 9).

Endoderm RT Signature

Genomic regions from the E-Endoderm signature (FIG. 1D) replicated early only in endoderm cell types and were enriched for genes from the FOXA1 transcriptional network (FIG. 9), including key activators in endoderm differentiation such as FOXA2, GSC, and PBX1.

Late Mesoderm RT Signature

Regions from the E-Late mesoderm signature replicated early only in late mesoderm (mesothelium, smooth muscle, myoblast, and fibroblast) and mesenchymal stem cells (FIG. 1D) and were enriched for genes involved in blood vessel, vascular, and muscle development as well as genes necessary for wound healing (FIG. 9).

Blood RT Signatures

Four distinct RT signatures for hematopoietic cell types were identified (FIG. 1D): (1) regions replicated earlier in all hematopoietic cell types (E-Blood); (2) regions only late in all hematopoietic cells (L-Blood); (3) regions only early in the myeloid lineage (E-Myeloid); and (4) regions only early in the lymphoid lineage (E-Lymphoid). The E-Blood RT signature contains genes involved in immune system and hemostasis pathways. The E-Myeloid RT signature was highly enriched in genes associated with signal transduction by GPCR, which plays a critical role during inflammation and immune processes, whereas the E-Lymphoid RT signature was enriched in genes involved in the regulation of lymphocyte activation (FIG. 9).

RT Switching Regions have Distinct Sequence Composition

Whether RT-switching regions and RT-constitutive regions have distinct DNA sequence composition (FIG. 2) was next examined. Consistent with previous reports in mouse and human cell types, constitutively early replicating regions were gene and GC-rich, with a lower density of LINEs and higher density of SINEs compared to constitutively late replicating regions, whereas RT-switching regions have intermediate sequence composition that exhibits a lower correlation with RT (FIG. 2B). However, unlike early mouse development, where the correlation of RT to GC and LINE content significantly increases during differentiation, correlations of DNA sequence features to RT did not change significantly between the cell types analyzed (FIG. 2B,C), including cell types very similar to the previously reported mouse cell types.

Temporal Consolidation and Deconsolidation of RDs and 'Stemness'

Figure 3A:
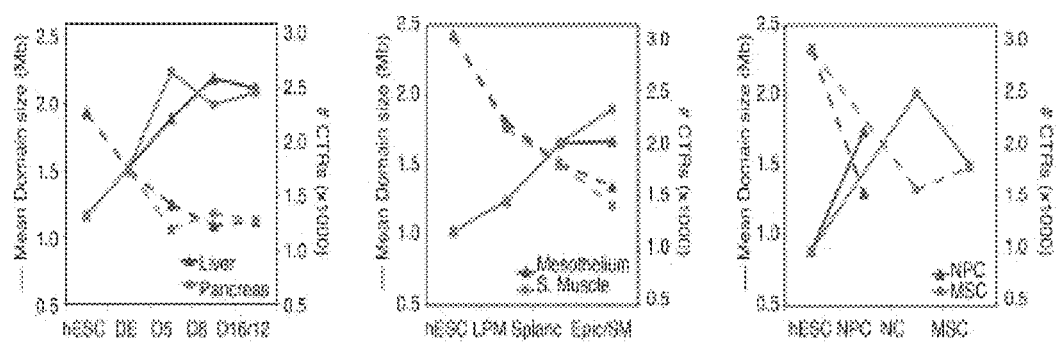
Figure 3B:
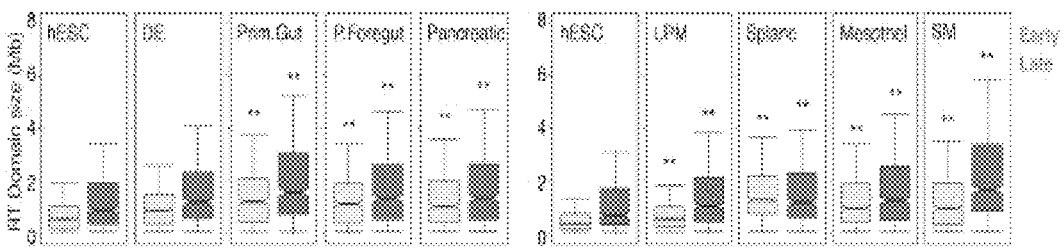

During differentiation of mouse and human ESCs, small differentially replicated RDs consolidate into larger regions of tandem RDs that replicate at similar times during S phase, termed constant timing regions (CTRs). Changes in global CTR organization were analyzed during the intermediate stages of hESC differentiation toward endoderm, mesoderm, and ectoderm (FIG. 3). Consistent with prior observations, a significant increase in the average CTR size together with a drop in the number of domains was observed in all differentiation pathways (FIG. 3A), both for early and late replicating regions (FIG. 3). Intriguingly, domain consolidation from ESCs to neural crest (NC) cells was followed by deconsolidation of both early and late domains on all chromosomes when NC cells were differentiated to mesenchymal stem cells (MSC) (FIG. 3) and recovered a portion of the ESC-like RT organization (FIG. 3D), suggesting that more discordant replication of adjacent RDs is a property of multipotency.

Dynamic Regulation of RT at the TSS during hESC Differentiation

Figure 4A:
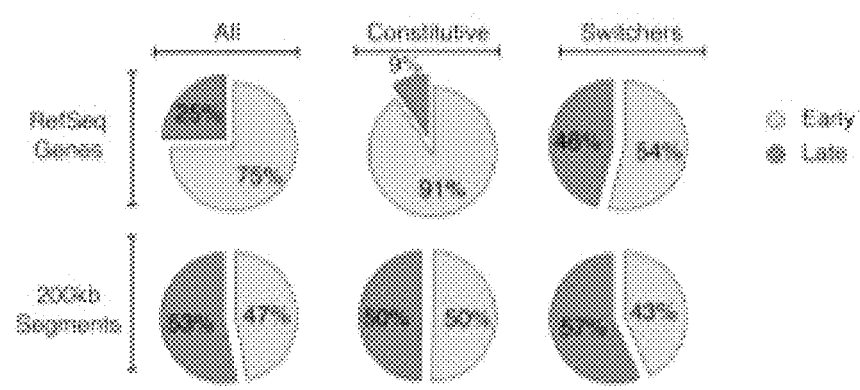
Figure 10:
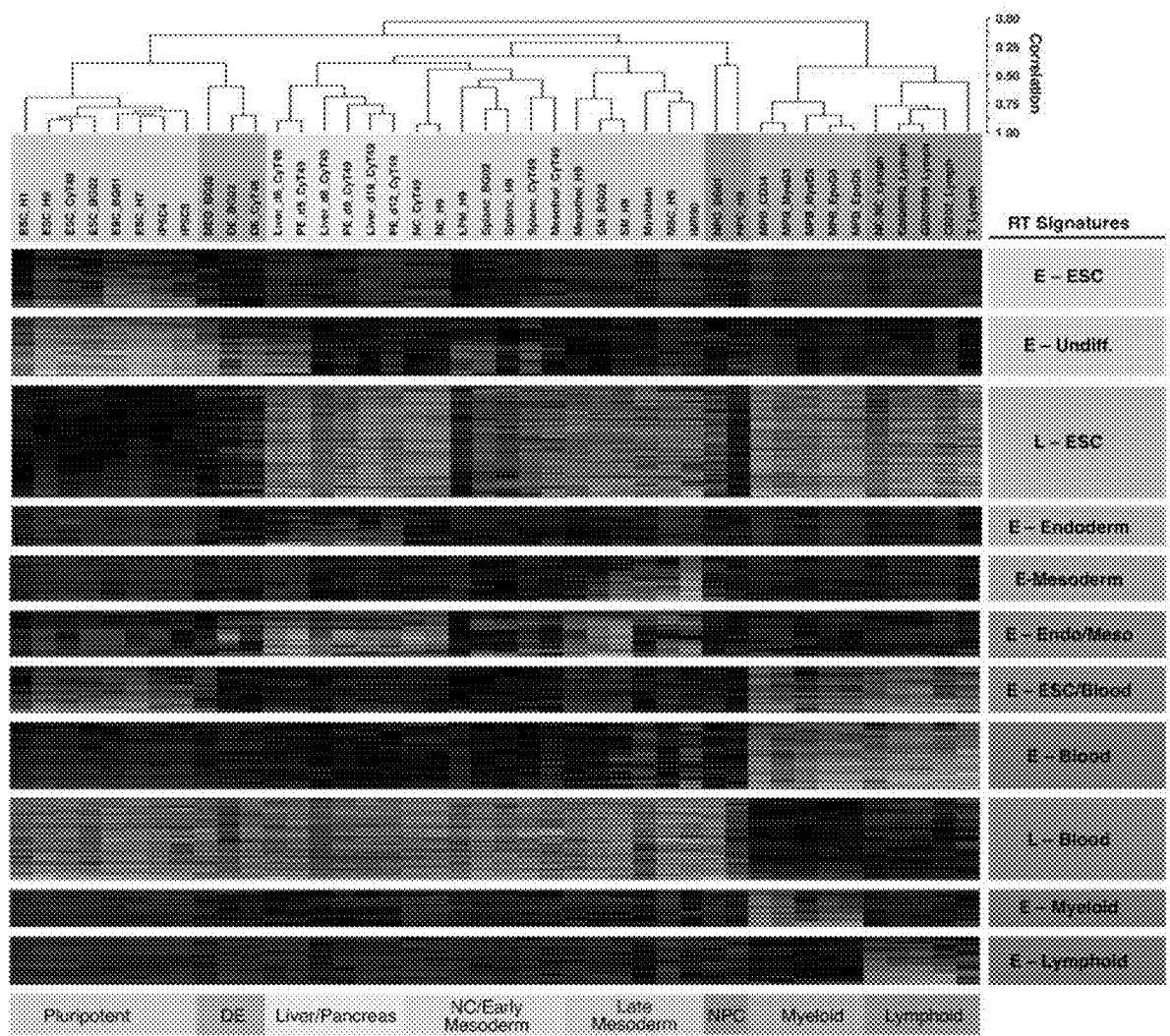
FIG. 10: Hierarchical clustering of the distinct human cell types and k-means clustering of RT-switching genes. RT-switching genes (27,544 RefSeqs) were used for hierarchical clustering analysis of the cell types and branches of the dendrogram were constructed based on the correlation values between distinct cell types (distance=correlation value−1). A correlation threshold of >0.6 was used to color label the major groups of cell types, specific cluster of cell types are indicated at the bottom: plutipotent, definitive endoderm, liver and pancreas, neural crest and early mesoderm, late mesoderm and fibroblasts, NPC, myeloid and lymphoid. k-means clustering of switching segments defined the RT signatures labeled in boxes.

To understand better how RT of coding genes is regulated during differentiation, transcription start sites (TSS) were focused on. RT ratios were obtained at the TSSs of 27,544 RefSeq genes (hg19 assembly), which were strongly correlated between replicates and averaged. RefSeq genes were classified into RT-constitutive and RT-switching genes using the same criteria as for 200-kb windows. Hierarchical clustering of the human lineages and k-means of the switching genes (FIG. 10) confirmed results obtained using the whole genome, and genes present in each RT signature overlapped with the associated genes from the clusters of 200-kb windows (FIG. 1). As expected, most genes were replicated during the first half of S-phase (74.7%) across all cell types independent of their transcriptional activity (FIG. 4A). In contrast, the subset of genes that switch RT during development was almost equally represented in early and late S-phase in all cell types analyzed, implying that a similar number of genes change Early to Late (EtoL) and Late to Early (LtoE) during differentiation (FIG. 4A).

Figures 4B, 4C, 4D:
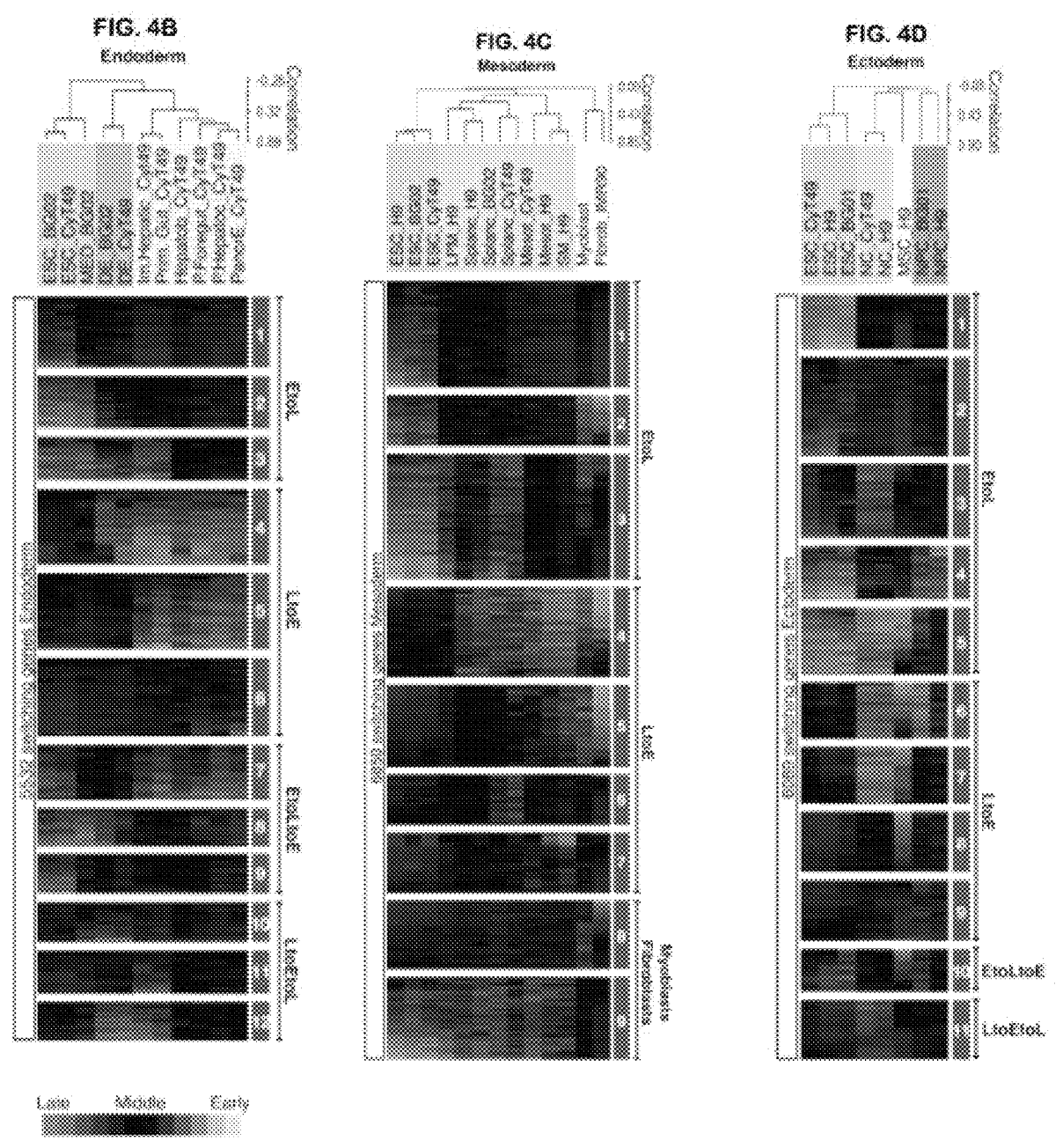

When separate differentiation pathways and their intermediate stages individually (FIG. 4B-D) were analyzed, distinct patterns of RT regulation emerged. First, consistent with mouse studies, many genes that switch from early to late replication (EtoL) during loss of pluripotency do so in all differentiation pathways, whereas genes switching from late to early (LtoE) are lineage specific and include regulators of key developmental transitions. However, analysis of differentiation intermediates identified genes switching transiently (EtoLtoE and LtoEtoL) during differentiation in specific lineages (FIG. 4B-D). Among the genes with transient changes LtoEtoL in RT were key regulators such as SOX17, a gene known to be involved in the differentiation toward endoderm cell types, whose expression is restricted to the transition stage of definitive endoderm.

RT and Transcription are Highly Coordinated during hESC Differentiation

Figure 4E:
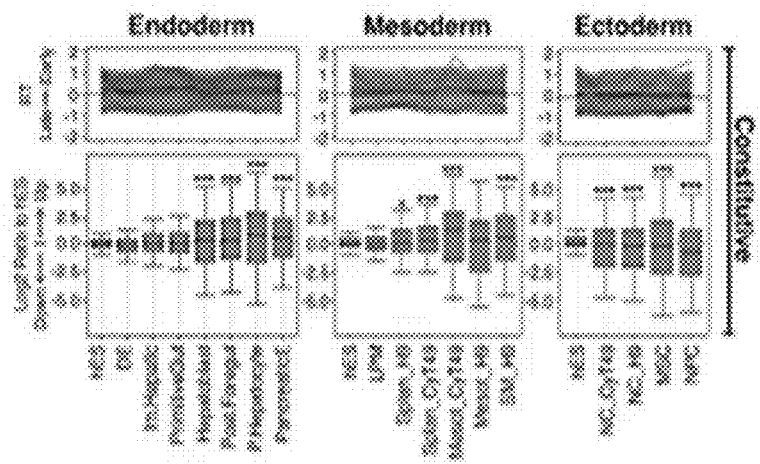
Figure 4F:
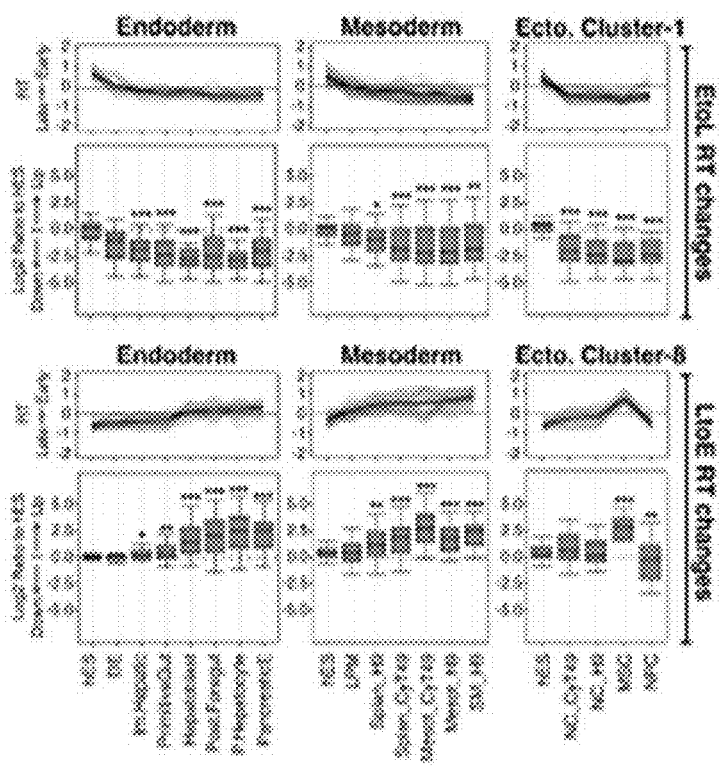
Figure 4G:
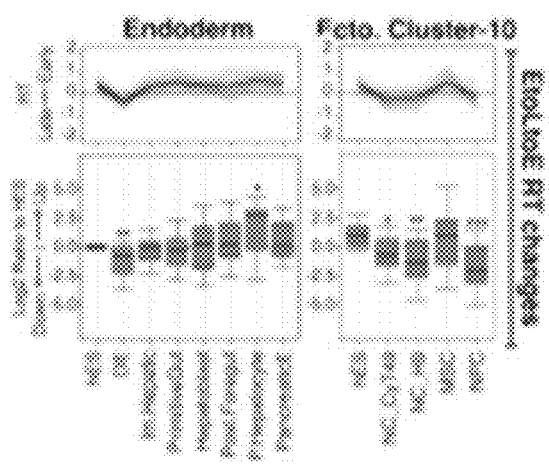
Figure 4H:
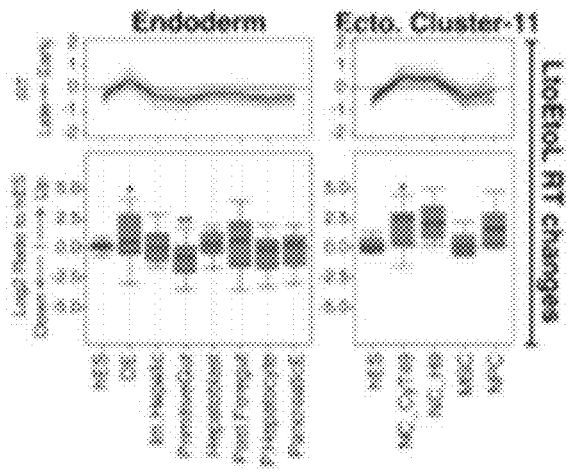

To analyze the relationship between RT and transcriptional regulation during differentiation, the transcriptomes of distinct cell types were obtained using HumanHT-12 v4 Illumina bead-based arrays. Analysis of specific markers confirmed the expression levels detected by array hybridization and the homogeneity of the distinct inter-mediate cell types. Next, genes that were induced or repressed during differentiation were classified by their RT changes (the cluster IDs identified in FIGS. 4B-D) and the kinetics of their transcription changes during differentiation. Transcription changes for RT-constitutive genes did not show enrichment for either induction or repression (FIG. 4E), whereas genes switching RT showed highly coordinated kinetics of RT and transcriptional changes in all differentiation pathways for all RT regulation patterns and cluster IDs (FIG. 4F-H).

Loss of Correlation between Gene Expression and RT during Differentiation

Figure 5A:
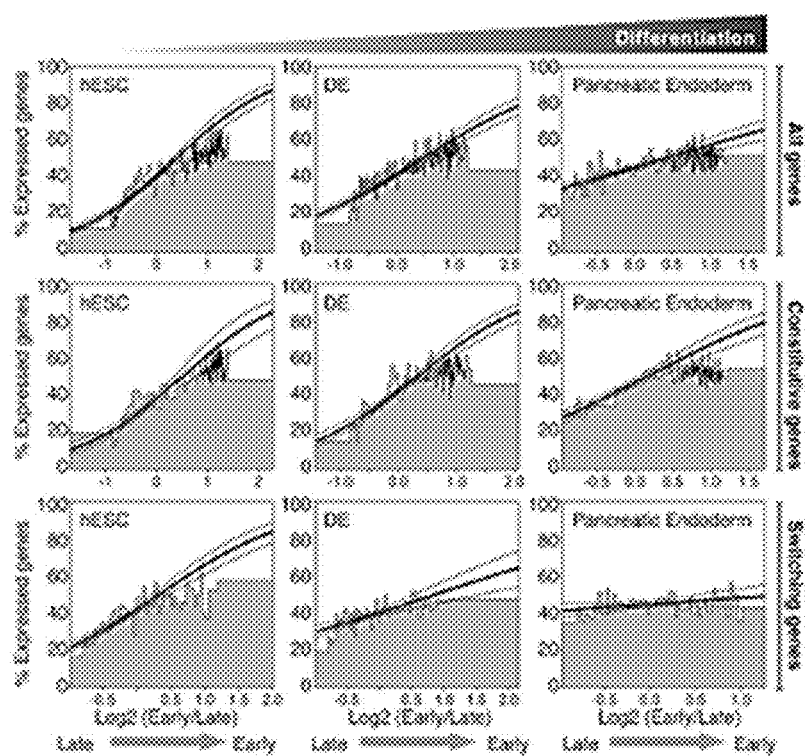
FIG. 5A, 5B, 5C, 5D: Switching genes and transcriptional regulation.

Perhaps the strongest correlation between transcription and early RT has been demonstrated by comparing the probability of transcription of genes (i.e., on or off) and their RT, something observed in all *Drosophila*, mouse, and human cell types examined. To investigate the degree to which this correlation is consistent across different cell types, genes were scored as either expressed (log 2 values>7.5) or not expressed. Surprisingly, it was observed that the correlation between early replication and gene expression declined during differentiation in every pathway (FIG. 5A). Moreover, although the correlation of RT and gene expression remained constant for RT-constitutive genes, RT-switching genes showed a weaker correlation that was almost completely lost during differentiation. Prior reports did not observe this loss in correlation during differentiation likely because they focused on neural lineages, which were the least affected by differentiation in the present studies. Hence, during differentiation, a decrease in correlation between early RT and transcription occurs that is driven by the behavior of RT-switching genes. These results raise a conundrum, since FIG. 4 demonstrates a strong temporal correlation between RT and transcription for these same genes.

Distinct Classes of RT-Switching Genes

Figure 5B:
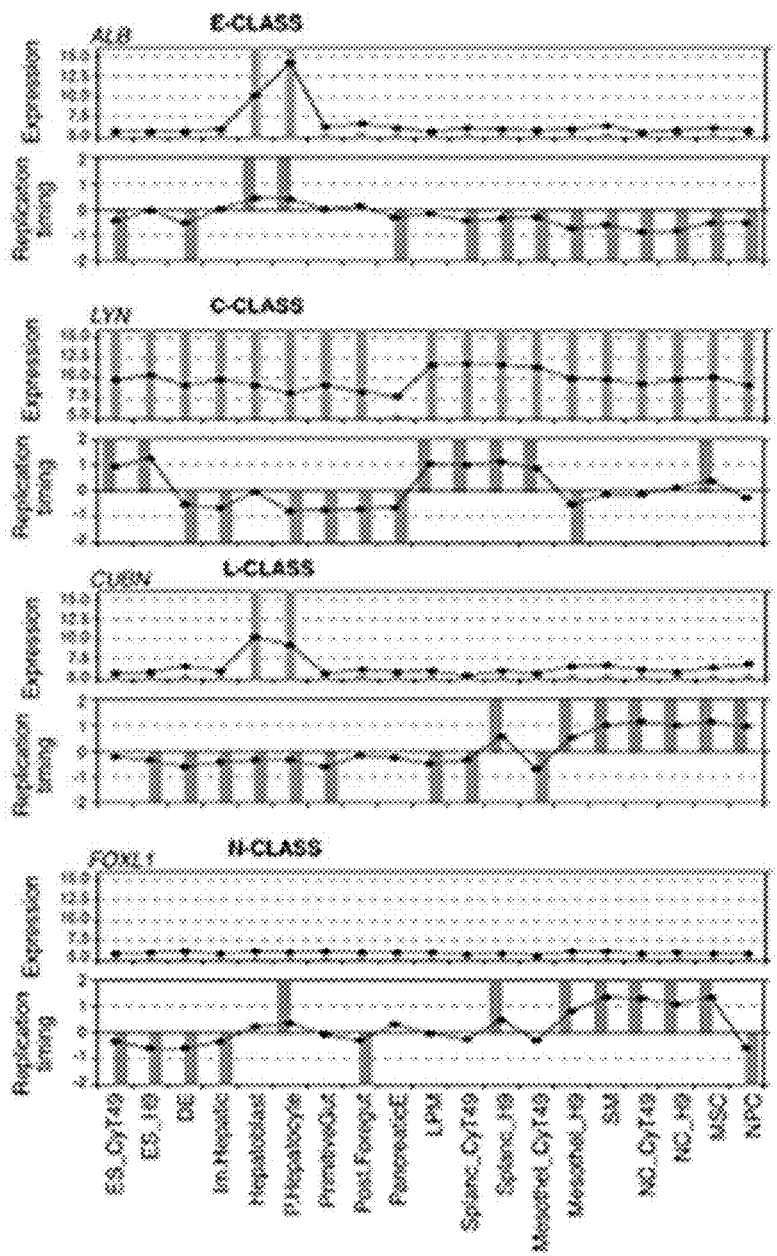
Figure 5C:
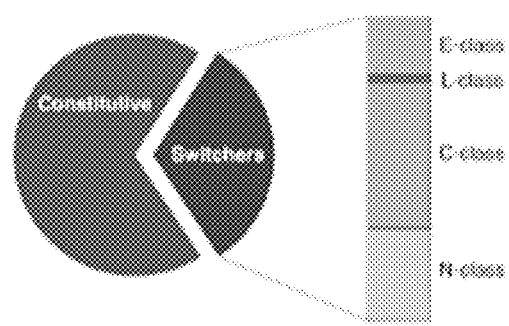
Figure 5D:
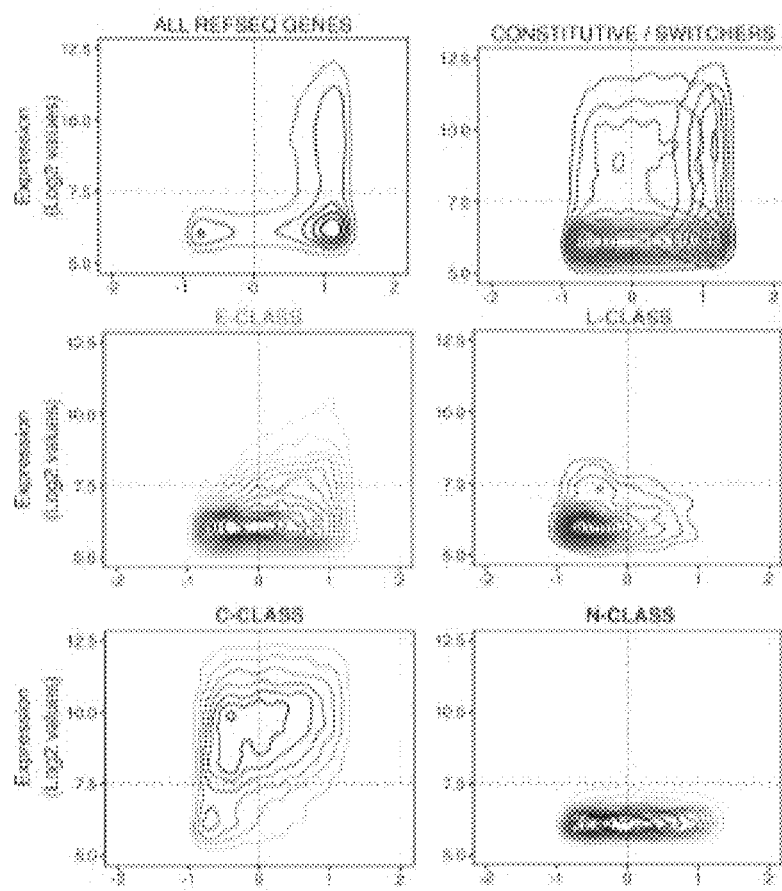

Next, the RT-switching genes were classified into distinct categories (FIG. 5B). E-class genes can be expressed only when they replicate early (no exceptions), whereas C-class were transcribed when late replicating in at least one cell type. L-class refers to a small number of RT-switching genes that were expressed only when replicated late. Finally, N-class genes were those that showed no detectable transcription activity in any profiled cell type and are presumably a mixture of C-, E-, and L-class. The RT-constitutive genes (that do not change RT) were classified as O-class genes. Interestingly, the C-class constituted the majority (47.6%) of RT-switching genes (FIG. 5C). C-class genes were expressed significantly higher than E- or L-class, and at comparable levels to O-class genes, regardless of their RT (FIG. 5D) and independent of cell type. It was previously demonstrated that the promoters of genes that were late replicating and expressed during mouse differentiation had a high CpG content, a property that has been implicated in differential gene expression. However, significant differences in the CpG content of these distinct classes of genes in humans were not found. A summary of the numbers of genes in each class and their RT regulation pattern (EtoL, LtoE, EtoLtoE, LtoEtoL) in different lineages was determined.

C-Class Gene Transcription is Frequently Coordinated with RT

Figure 6D:
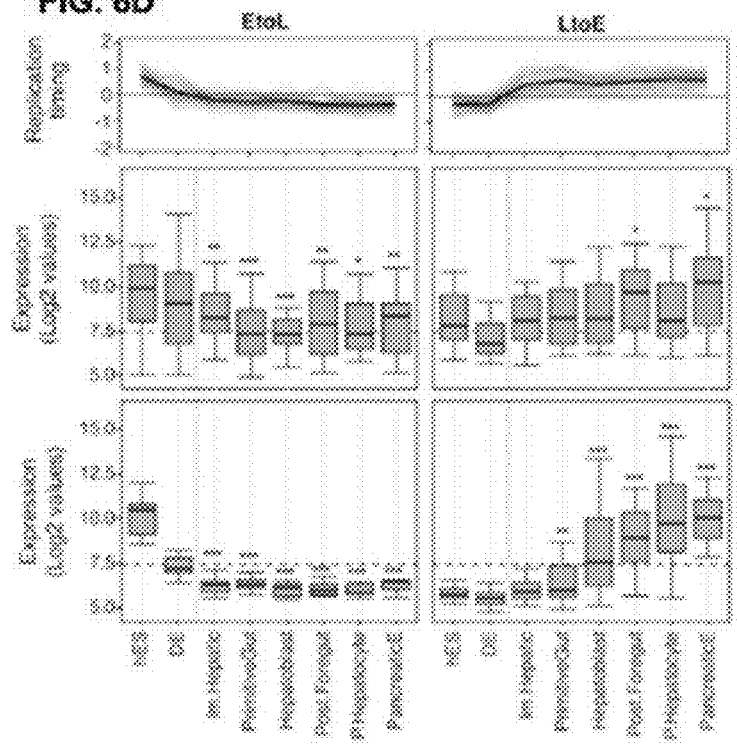
Figure 6E:
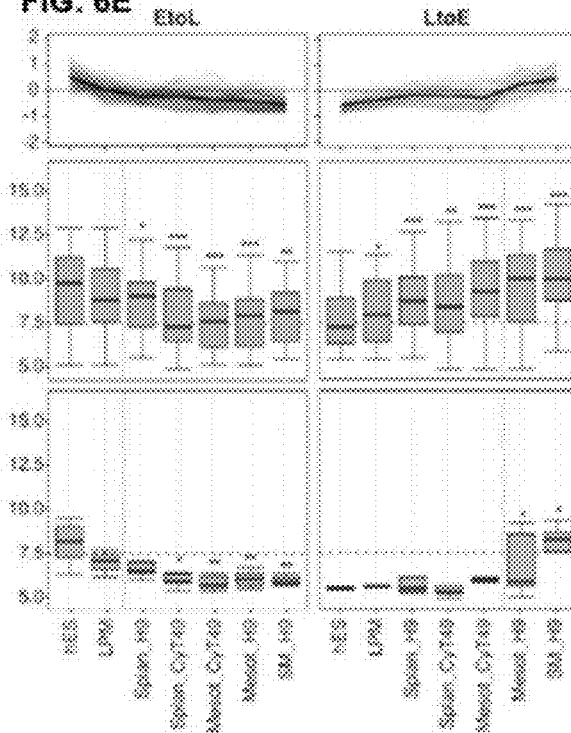

The results above demonstrate highly coordinated changes in transcription and RT for C-class genes (FIG. 4F-H), despite a lack of correlation between RT and gene expression (FIG. 5). One explanation for this discrepancy is if C-class genes are only highly transcribed in cell lineages in which the genes switch to early RT, but their expression in intermediate stages precedes or follows the RT switch. To investigate this possibility, the RT changes were subclassified as either gradual, with middle replication (EtoMtoL or LtoMtoE) (RT log 2 ratio >−0.3 and <+0.3) identified in an intermediate stage (25% of cases), or abrupt, without a middle replication intermediate (75% of cases). The analysis of changes in C-class transcription was then restricted to the cell type intermediates just before and after abrupt versus gradual RT switches. This resulted in a complete absence of correlation of early replication to transcription (FIG. 6A-C). Next, the kinetics of transcriptional and RT changes during differentiation in the three main germ layers were analyzed. C-class genes followed the same dynamic changes in gene expression as E-class genes, except that transcriptional up-regulation often preceded the LtoE switch while a decrease in transcription often occurred after the EtoL RT switch (FIG. 6D-F). Thus, the subset of C-class genes that change transcription were induced when late, primarily during a window of differentiation that closely precedes or follows the RT switch.

One concern was that high expression of a gene in a small percentage of cells replicating that gene early would be misclassified as a C-class gene. This seemed unlikely given the homogeneity of markers for each intermediate stage observed in experiments performed as described herein and by others and the fact that similar results were observed in all lineages. Moreover, some of the C-class genes were expressed to similarly high levels in all cell types across many switches in RT, so it would be unlikely to have contaminating cells in every one of these cell types. More directly, for those C-class genes for which transcriptional up-regulation preceded the LtoE switch or those for which a decrease in transcription occurred after the EtoL RT switch, it was frequently seen that the level of induction of transcription reached or remained at its maximum level before or after the RT switch, respectively. If expression were due to contaminating early replicating cells, transcription would continue to increase with the increase in the percentage of early replicating cells, and this was not the case. The difference between C-class and E-class was also not due to the level of transcriptional induction because many E-class were induced to similar levels as the C-class genes.

An alternative explanation for C-class gene behavior could be asynchronous replication between gene homologs, with one homolog replicating early and expressed. However, very few loci in mammalian genomes display asynchronous replication, and so far all of them have been linked to either X Chromosome inactivation in female cells or to parental imprinting/monoallelic gene expression. Moreover, direct comparison of known asynchronously replicated or monoallelically expressed genes to the present categories of genes revealed that such genes are mostly constitutively replicated. It is also unlikely that C-class genes are becoming asynchronous uniquely in the lineages where their up-regulation was seen, because one can detect a significant shift in replication timing even of a single homolog (e.g., the inactivated X Chromosome), and 75% of the replication timing shifts detected were single abrupt shifts without intermediate replication times. Together, these results are most consistent with the conclusion that a high level of transcription for many (not all) C-class genes is coordinated with early RT but can precede or follow the RT switch.

C-Class Genes are Key Regulators in TRNs

The fact that RT switches are frequently preceded by induction of C-class genes (FIG. 5) and followed by induction of E-class genes (FIG. 6D-F) suggests the hypothesis that C-class might drive the RT switches required for expression of E-class genes. One prediction of this hypothesis is that C-class genes should have a higher hierarchy in transcriptional regulatory networks (TRNs). Available human TRNs (Gerstein et al. 2012) were used to compute the interclass regulation probability and it was found that C-class genes are most central and regulate all three classes of genes (C-class, E-class, and O-class) (FIG. 6G). Notably, E-class genes are least central and regulated mainly by C-class genes (FIG. 6G). Together these results suggest a central role for C-class genes in the regulatory interactions during differentiation and a subordinate role for E-class.

Developmentally Regulated Changes in RT Occur at RD Boundaries

To better understand the differences between distinct classes of genes, their positions relative to the boundaries of the RDs were analyzed. First, timing transition regions (TTRs) were identified in all the cell types profiled based on changes in the slope of RT profiles, using a previously described algorithm (Pope et al. Nature 515: 402-405 (2014)), and the TSS of each category of genes was aligned to the RD boundaries (defined as the earliest replicating border of TTRs) (Pope et al. Nature 515: 402-405 (2014)). As expected, RT-constitutive genes (O-class) were highly enriched throughout early replicating RDs; in contrast, it was found that switching genes were enriched at the RD boundaries (FIG. 6H,I). L-class genes were preferentially located in late domains. No clear differences were observed between C-class, E-class, and N-class genes—all three categories of switching genes were highly enriched at RD boundaries (FIG. 6H,I). These results are consistent with previous evidence suggesting that changes in RT might be associated with differential activation of replication origins in close proximity to TTRs.

Discussion

Genome-wide RT profiles were generated for 26 different cell types and distinct intermediate stages of endoderm, mesoderm, ectoderm, and neural crest differentiation, permitting changes in transcription and RT to be tracked during transitions between intermediate cell types in several cell lineages. In addition to providing a resource of genomic segments subject to RT regulation during development, these results revealed that the longstanding correlation between early replication and transcription does not hold for most "RT-switching genes," which are up-regulated just prior to a switch from late to early replication and down-regulated just after the switch from early to late replication. A class of genes was also identified that are expressed only in cell types where they are replicated late. These results reveal previously unappreciated complexities in the relationship between RT and gene expression.

RT and Transcriptional Control

Changes in RT occur in segments of 400-800 kb known as replication domains (RDs) that consist of stable structural units of chromosomes detected as self-interacting structural domains by Hi-C and referred to as TADs. Genes within RD/TADs can be classified into those that switch RT during differentiation (RT-switching genes) and those that do not (RT-constitutive genes or O-class). Here, the relationship between RT and transcription in each of these categories of genes was examined. Almost all RT-constitutive genes are early replicating, highly expressed, and show a much greater breadth of expression (expressed in more tissues) than the rare constitutively late genes. RT-constitutive RD/TADs also exhibit a strong correlation between early replication and their chromatin nuclease sensitivity. RT-constitutive genes thus adhere to the longstanding notion that early replication is associated with open chromatin and transcriptional activity, albeit late replication does not preclude a low level of transcription for a small number of genes. Approximately one-third of RT-switching genes were expressed uniquely when early replicating (E-class). However, the majority of RT-switching genes were expressed to very high levels, even when late replicating (C-class), and showed a breadth of expression similar to O-class (RT-constitutive genes). Interestingly, RT-switching RD/TADs are also among the most resistant to nuclease attack in the genome, regardless of RT. Findings with developmental-regulated RDs then, which represent a substantial fraction of the genome (as stringently defined here, they encompass >30% of the genome), indicate that late replication and closed chromatin are not incompatible with high levels of transcription, challenging the longstanding notion it has been demonstrated has been driven primarily by constitutive RDs.

Unlike prior studies of mouse ESC differentiation, the hESC differentiation systems described here are sufficiently synchronous and homogeneous to permit one to track RT and transcription during intermediate stages of differentiation. First, it was found that the correlation between RT and the probability of a gene being called "ON" or "OFF" dropped considerably during differentiation to almost no correlation in most cell types. This loss of correlation was accounted for largely by the C-class genes, which can be expressed in many broad cell types when replicated late. However, RT and gene expression changes were generally coordinated for all genes in all tracked lineages. Despite their ability to be transcribed at high levels when late replicating, transcription of C-class genes was indeed still coordinated with RT, but increased just prior to an LtoE switch and was down-regulated just after an EtoL switch. Frequently, the induction of E-class genes, which follows LtoE RT changes, is preceded by up-regulation of C-class genes from within the same developmental RD. Two representative examples are shown in FIG. 6J: C-class genes are expressed at low levels in late replicating regions, they are up-regulated during differentiation just prior to an LtoE switch, after which the E-class genes—GC, ST3GAL1, and WISP1—begin transcription.

Figure 7:
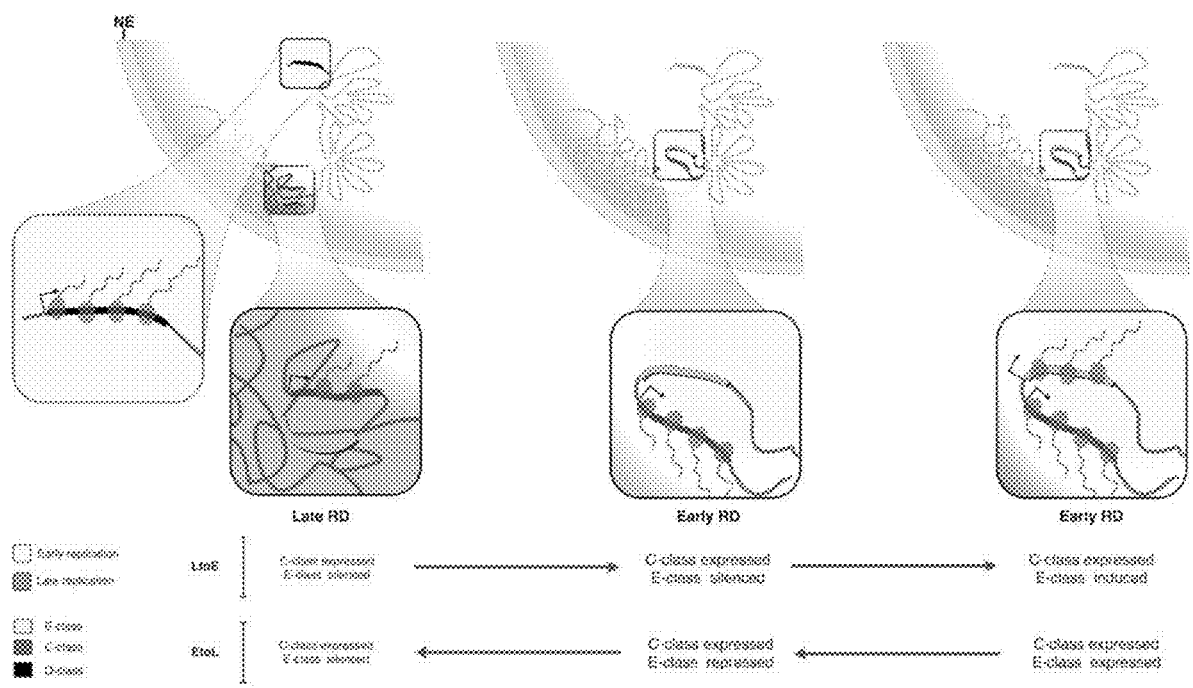
FIG. 7: RT and transcriptional control. Early replication occurs in the nuclear interior, while late replicated regions are positioned at the periphery. Two RDs illustrate the differences in organization of early and late replicated regions. Transcriptional activity and chromatin organization of E- versus C-class genes are represented in the expanded pictures during EtoL and LtoE RT changes.

RT has been linked with the nuclear organization of chromatin, with early replicated regions located at the nuclear interior and late replicating regions associated with the nuclear lamina. The transcriptional potential of C-class genes regardless of their RT (FIG. 5) and their preferential position within TTRs (FIG. 6H,I), together with their central position in the TRNs (FIG. 6G), suggest an intriguing model of RT and gene expression regulation during cell fate specification that helps to understand the complex relationship between RT and transcription (FIG. 7). In this model, early RDs are located at the nuclear interior in closer proximity to regions of active transcription. In contrast, late RDs are positioned close to the periphery, in a compartment that is less permissive for transcription. Genes located at the early RDs can be expressed at high levels at any stage of differentiation. However, only C-class genes can be expressed to high levels when located within late RDs. This may have to do with specialized features of the regulatory elements of these genes allowing them to be expressed within late replicating chromatin. Alternatively, regulatory elements of C- and E-class genes may reside in different 3D orientations within the RD/TADs. In this model (FIG. 7), up-regulation of the C-class gene triggers an LtoE change in RT and movement to the nuclear interior, which permits the E-class gene to be expressed. This model makes the testable prediction that preventing C-class gene induction will prevent early replication and E-class gene expression.

Methods

Cell Culture and hESC Differentiation hES cell lines (CyT49 and H9) were differentiated using defined media specific for each pathway (Schulz et al. Neurosci 4:27 (2003); Menendez et al. Proc Natl Acad Sci 108: 19240-19245 (2011); Menendez et al. Nat Protoc 8: 203-212 (2013)).

Purification of Normal Hematopoietic Progenitors and in vitro Differentiation toward Myeloid/Erythroid Lineages CD34+ cells were provided by the Yale Center for Excellence in Molecular Hematology, stimulated to proliferate and differentiate in vitro toward myeloid and erythroid lineages according to established protocols.

Genome-Wide RT profiling

Genome-wide RT profiles were constructed as previously described by array hybridization (Hiratani et al. PLoS Biol 6: e245 (2008); Ryba et al. Nat Protoc 6: 870-895 (2011)). Previously, it was shown that array hybridization (Replichip) and NGS (Repli-seq) produce indistinguishable results. Published RT data sets from hESC (cell lines BG01, BG02, H7, and H1), iPSC, NPC (derived from hESC BG01), mesendoderm and DE (derived from hESC BG02), smooth muscle (from hESC BG02), myoblasts, and fibroblast and lymphoid cells were included in the analysis. RT data sets were normalized using the limma package (Smyth (2005) limma: linear models for microarray data. In Bioinformatics and computational biology solutions using R and bioconductor (ed. Gentleman R, et al.), pp. 397-420. Springer, N.Y.) in R (R Core Team (2015) R: a language and environment for statistical computing. R Foundation for Statistical Computing, Vienna, Austria) and rescaled to equivalent ranges by quantile normalization).

Clustering Analysis

Hierarchical and k-means clustering analysis were performed using Cluster 3.0 (de Hoon et al. Bioinformatics 20: 1453-1454 (2004)). Uncentered correlation metrics and average linkage were used for clustering analysis in FIGS. 1 and 3, but standard correlation and Euclidean distances produced similar results. Heatmaps and dendrograms were generated in JavaTreeView (Saldanha Bioinformatics 20: 3246-3248 (2004)). Sex chromosomes as well as pericentromeric and subtelomeric regions were removed from the analysis.

Gene Expression Analysis

Total RNA was extracted, labeled, and hybridized to HumanHT-12v4 Expression BeadChips (Illumina, Inc.).

Identification of Constant Timing Regions (CTRs)

Segmentation of genome-wide RT profiles into CTRs was performed as previously described (Hiratani et al. PLoS Biol 6: e245 (2008); Ryba et al. Nat Protoc 6: 870-895 (2011)) using DNAcopy, version 1.36.0 (Venkatraman and Olshen Bioinformatics 23: 657-663 (2007)), in R to identify the regions with uniform y-axis values. To account for the dependency of segmentation on slight differences in autocorrelation of neigh-boring probes between data sets, Gaussian noise was applied to equalize their autocorrelation (ACF) before segmentation.

Identification of RD Boundaries

Loess smoothed RT profiles were obtained from each quantile-normalized data set, and RT boundaries were obtained as previously described (Pope et al. Nature 515: 402-405 (2014); Yue et al. Nature 515: 355-364 (2014)).

Briefly, RD boundaries were identified as the early border of transitions between relatively earlier and later replicating regions (TTRs) in individual data sets with a slope above $\pm 2.75 \times 10^{-6}$ RT units/bp at the early border and with a sustained slope above $\pm 1 \times 10^{-6}$ RT units/bp for at least 250 kb.

TRN Analysis

RT and gene expression data were used to classify genes into E-class, C-class, and O-class based on the values of three variables: replication time (RTC) and switch (SC) cutoffs, defined as in FIG. 8; and stringency cutoff (PCT), defined as the percentage of cell types in which the gene is expressed. Transcription regulatory networks were then used to compute the inter-class regulation probability. For each pair of classes, the number of edges connecting genes from each class was counted. This number was divided by the number of possible edges, which is the product of the class sizes.

Data Access

Replication timing and transcriptome data from this study have been submitted to the NCBI Gene Expression Omnibus (GEO) under accession numbers GSE63428 and GSE63592, to ENCODE portal, and are also publicly downloadable and graphically displayed (Weddington et al. BMC Bioinformatics 9:530 (2008)).

Example 2

Alterations in DNA Replication Timing Identify TP63 as a Novel Marker of Progeroid Diseases Progeroid syndromes are rare genetic disorders that phenotypically resemble natural aging. Despite identification of causal mutations, mechanisms that generate their clinical manifestations remain elusive. Here, a DNA replication timing (RT) signature was identified that distinguishes progeroid syndromes from normal aging and identifies TP63 gene as a new disease marker. Abnormal TP63 RT appears early during differentiation of progeroid iPSCs and is associated with altered gene variant expression. These findings demonstrate the utility of RT signatures to identify novel biomarkers not detected by other methods, reveal abnormal TP63 RT as an early event in progeroid disease progression and offer TP63 gene regulation as a potential therapeutic target.

Previously, it was demonstrated that the temporal order in which the genome is duplicated, known as the replication-timing (RT) program, is closely linked to spatial organization of chromatin (Pope, B. D. et al. Nature 515, 402-405 (2014)) and is regulated during development in coordination with gene activation (Rivera-Mulia, J. C. et al. Genome Res. 25, 1091-1103 (2015); Rivera-Mulia, J. C. & Gilbert, D. M. Curr. Opin. Cell Biol. 40, 168-178 (2016)). Hence, RT constitutes a readily measurable functional readout of large-scale chromatin organization and transcriptional potential that can be exploited to detect alterations in nuclear organization and function in disease. Here, HGPS fibroblasts were analyzed to determine if the RT program is altered in the disease. Moreover, since multiple symptoms of HGPS have been associated with the broad phenotype observed in physiological aging, the extent to which RT alterations in progeria are associated with the RT changes observed during normal aging was examined. Additionally, whether the RT abnormalities observed in HPGS are shared with other progeroid syndromes (e.g. RTS) was examined. A progeroid-specific RT signature was identified that contains genomic regions that replicate early only in the cells derived from progeroid diseases but late in fibroblasts from healthy individuals across a wide range of ages. Among the RT abnormalities in HGPS, TP63 was identified as a new gene marker for progeroid syndromes. Alterations in TP63 regulation have not previously been observed in patients with progeroid syndromes but mutations of the gene are associated with other diseases that share some clinical manifestations. Additionally, when cells derived from HGPS and RTS patients were reprogrammed to iPSCs all RT differences with normal cells were erased, but when re-differentiated back to fibroblast cells, abnormal RT of TP63 re-appeared suggesting that this change is an early epigenetic event in the progression of progeroid diseases. Moreover, the TP63 RT abnormality in progeroid syndromes was associated with an altered ratio of TP63 gene variants, which has been previously linked to cellular senescence defects and abnormal developmental regulation of epithelial progenitor cells. These results implicate TP63 in the progression of progeroid disease, suggest a provocative link between abnormal RT and altered gene variant expression and demonstrate the utility of RT profiling to identify novel avenues in disease research.

RESULTS

Replication Timing Abnormalities in HGPS

Figure 11A:
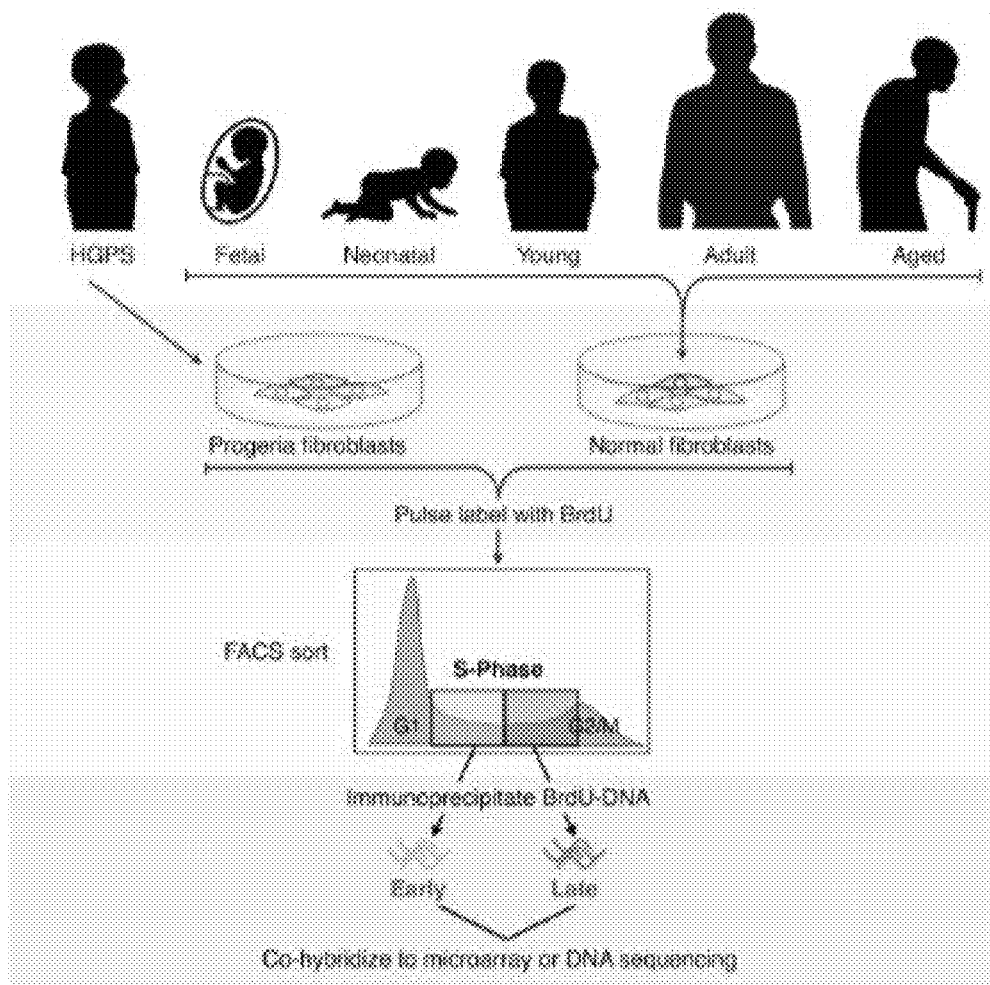
Figure 11B:
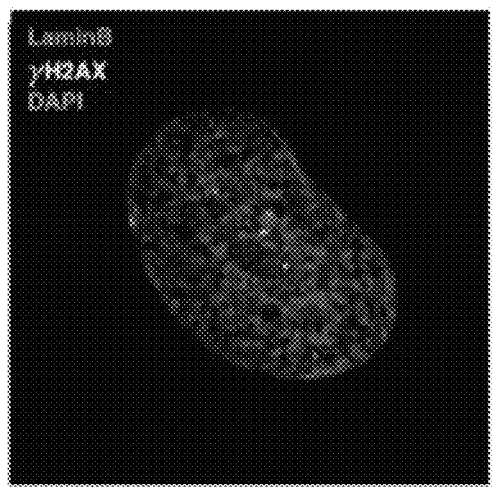
Figure 11B:
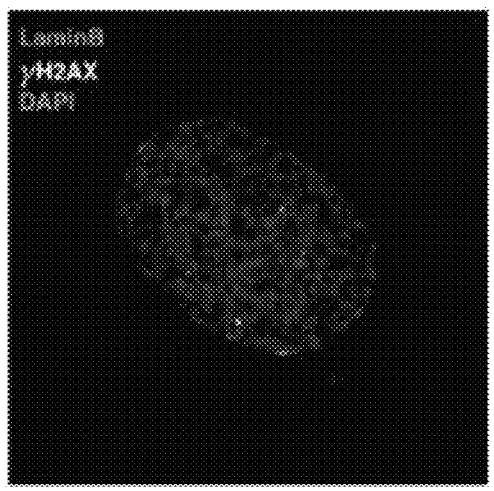
Figure 11C:
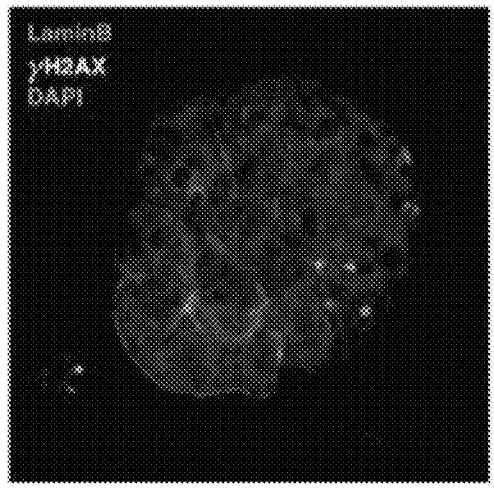
Figure 11C:
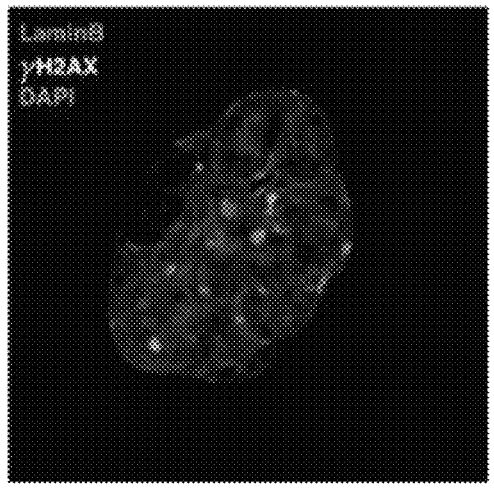
Figure 11E:
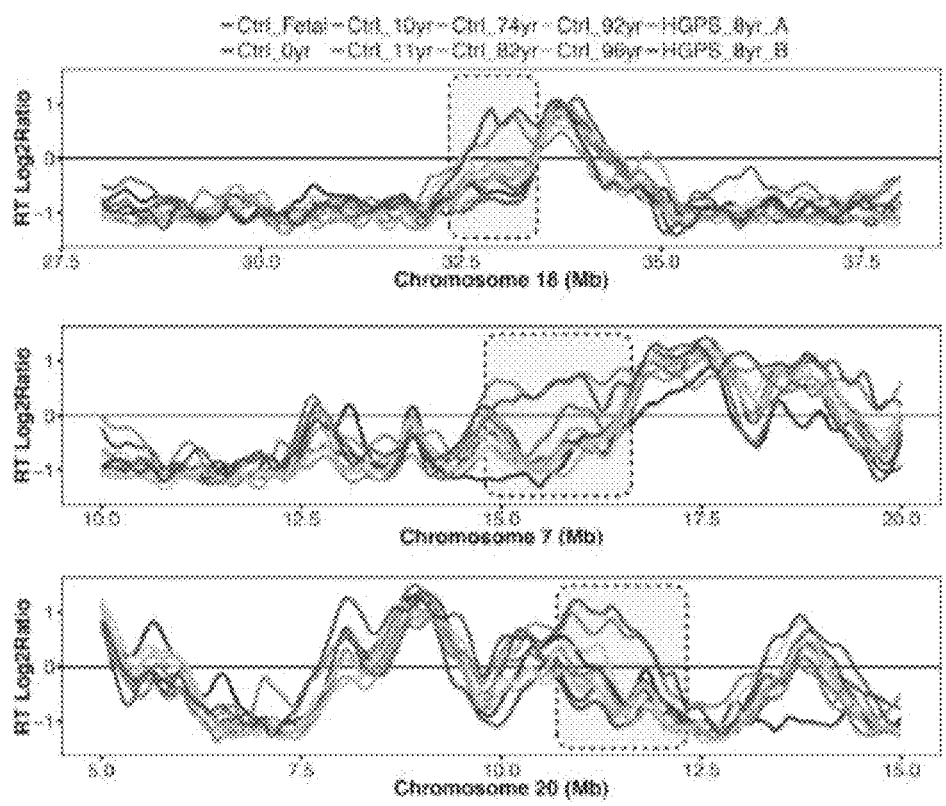

To determine whether the RT program is altered in HGPS, 61 genome-wide RT datasets of fibroblasts derived from patients and healthy donors across different ages (FIG. 11(a)) was generated as previously described (Ryba, T et al., Nat Protoc 6, 870-895 (2011); Marchal, C. et al. Repli-seq: genome-wide analysis of replication timing by next-generation sequencing. (2017) doi:10.1101/104653). Previous studies observed similar alterations in 3D chromatin organization between cells from HGPS donors and cells undergoing in vitro-induced senescence. Therefore, RT in cells entering replicative or oncogene-induced senescence was also analyzed. The characteristic nuclear abnormalities of HGPS cells were observed, such as altered nuclear envelope morphology and an increase in number and size of phosphorylated H2AX (γH2AX) foci associated with DNA damage when compared with cells from healthy donors (FIG. 11(b), 11(c)). Consistent with previous findings demonstrating that the RT program is cell type specific and a highly stable epigenetic property resistant to distinct perturbations, strong genome-wide correlations of RT (r>0.75) between all samples were found. Nonetheless, progeria cells were separated from normal fibroblasts, albeit correlated more with the cells from the oldest healthy donors (FIG. 11(d)). Overall, RT differences observed in progeria, natural aging and cellular senescence comprise 7% of the autosomal genome with distinct RT changes specific for the HGPS disease that are not associated with natural aging or cellular senescence (FIG. 11(d), 11(e)).

A Specific RT Signature Distinguishes HGPS Cells

Figure 12A:
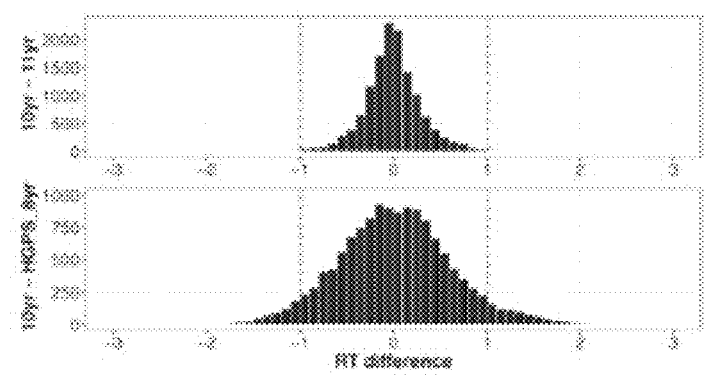
FIG. 12A, 12B, 12C, 12D, 12E, 12F: Identification of a replication timing signature HGPS-specific.
Figure 12B:
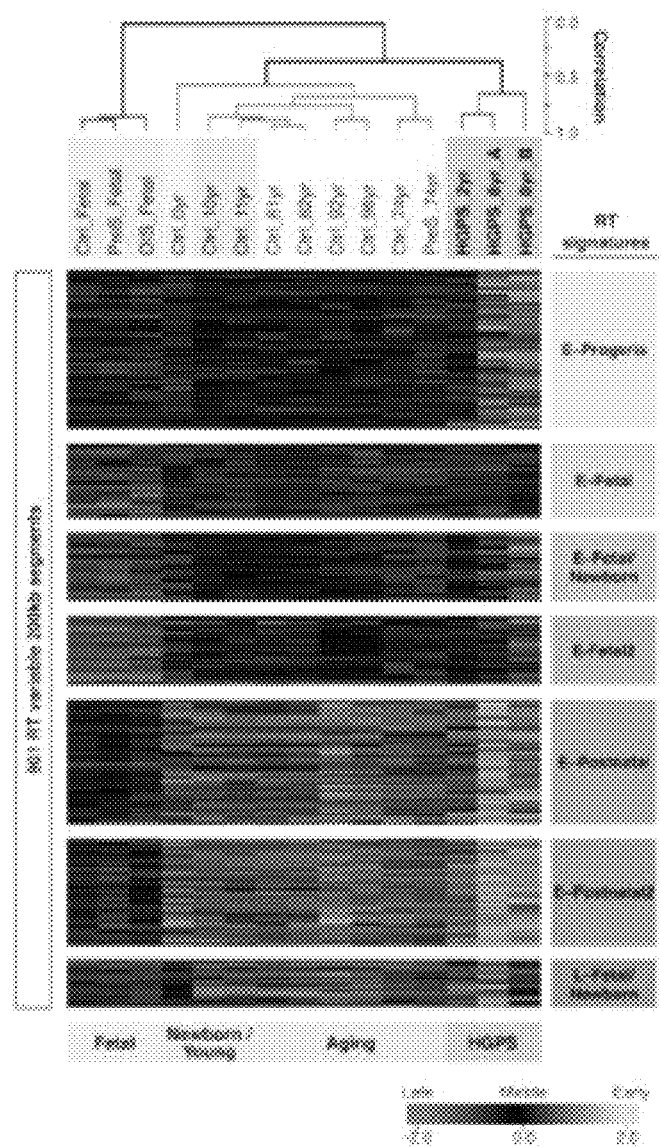
Figure 12C:
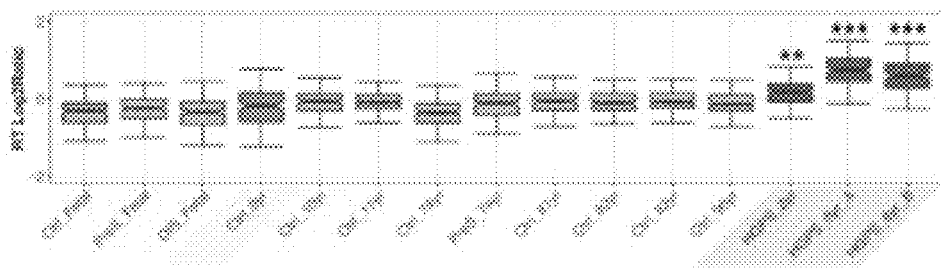
Figure 12D:
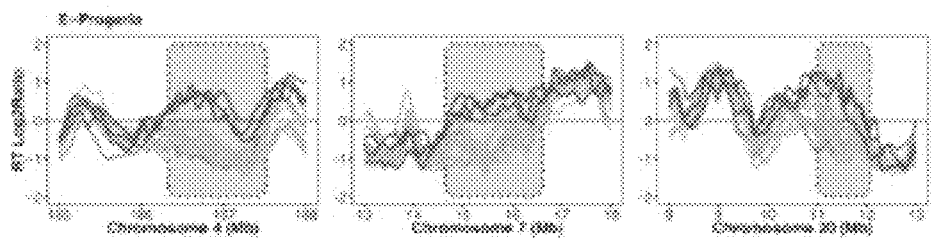
Figure 12E:
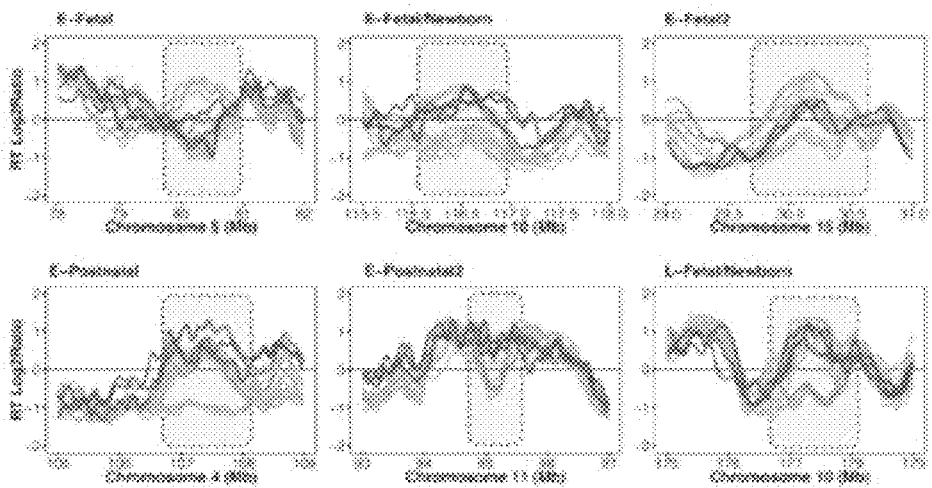
Figure 12F:
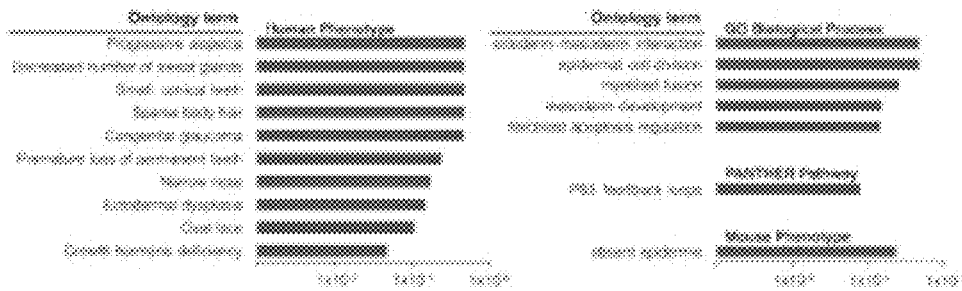

Previously, cell type-specific RT signatures in 26 normal cell types were identified and it was found that changes towards earlier replication are associated with transcriptional induction, while changes towards later replication correlate with gene repression during human development (Rivera-Mulia, J. C. et al. Genome Res. 25, 1091-1103 (2015)). Here, all RT-variable genomic segments were identified and RT signatures between fibroblasts of different age or disease-groups were identified. Briefly, genome-wide RT profiles were expressed as numeric vectors of 13,305 average RT ratios for non-overlapping 200 kb windows and variable regions were identified based on the RT log 2 ratio changes across the samples (FIG. 12(a)). Three major clusters were found that separate the samples into fetal fibroblasts, healthy post-natal (0-96 yr) and HGPS cells (FIG. 12(b)). Moreover, a specific RT signature containing regions that replicate early only in progeria fibroblasts but later in cells from all healthy donors (E—Progeria) was identified, including natural aging and cells at the entry to cellular senescence (FIG. 12(b)-12(d)). Additional RT signatures identified major differences between fetal cells and fibroblasts from all postnatal donors (FIG. 12(b), 12(e)). To determine the biological significance of the progeria-specific RT signature and its relationship to disease pathogenesis, gene ontology (GO) analysis was performed. Results revealed that regions that replicate early in HGPS are enriched in genes whose abnormalities are associated with the main phenotypic characteristics of the disease (FIG. 12(f)). Surprisingly however, none of the ontology terms have been associated with progeroid syndromes, but rather were annotated in distinct diseases (Köhler, S. et al. The Human Phenotype Ontology project: linking molecular biology and disease through phenotype data. 42, D966-74 (2014)), which nonetheless share some phenotypic characteristics with HGPS: hypodontia, small and conical teeth, alopecia, narrow nose and growth hormone deficiency among others.

TP63 is a New Marker of HGPS

Figure 13A:
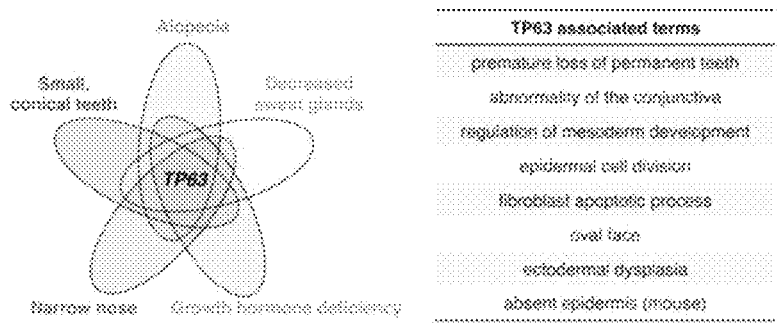
FIG. 13A, 13B, 13C, 13D: TP63 gene is a new marker of HGPS.
Figure 13B:
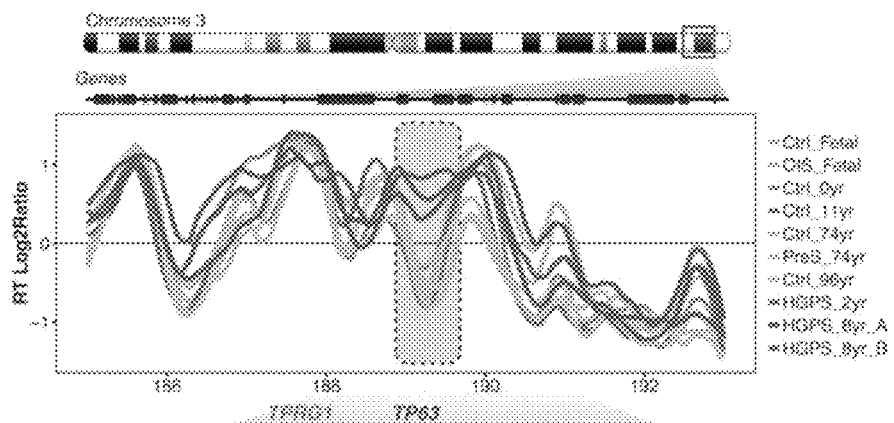
Figure 13C:
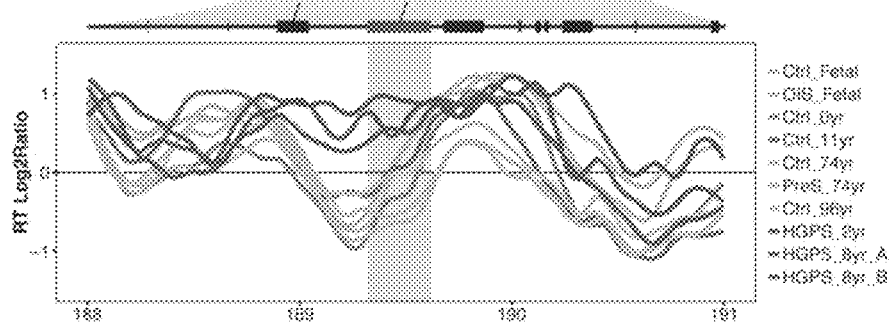
Figure 13D:
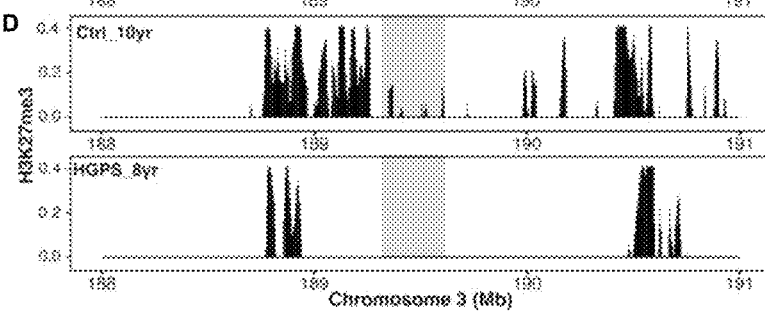

To identify new candidate markers of HGPS, the genes within the GO terms associated with the progeria-specific RT regions were examined. Overlap analysis of ontology terms revealed a unique common gene: TP63, which encodes for the tumor suppressor protein p63, as a potential new marker associated with the HGPS phenotype (FIG. 13(a)). RT profiles at the TP63 locus confirmed that the region replicates early only in progeria cells but late during S-phase in fibroblasts from all healthy donors regardless of their age (FIG. 13(b), 13(c)). Since changes from late to early replication are correlated with transcriptional induction, abnormal RT of TP63 in progeria cells might be associated with altered gene regulation of the TP63 gene. Consistently, a depletion of the repressive H3K27me3 epigenetic mark is observed at the TP63 locus in HGPS cells when compared with healthy donors of similar age (FIG. 13(d)). Moreover, RT alterations in HGPS include the upstream region of TP63, which is also depleted of H3K27me3 in HGPS cells (FIG. 13(d)) and contains a locus that encodes for the TP63-regulated 1 (TPRG1). The function of TPRG1 is still unknown but it is highly expressed in normal skin tissue and is regulated by TP63.

The TP63 gene is a member of the p53 family and encodes multiple variant protein isoforms with distinct functions (Paris, M. et al., Cell Death Differ 19, 186-193 (2011); Vanbokhoven, H. et al., Journal of Investigative Dermatology 131, 1196-1207 (2011)). Alternative promoters drive the expression of the main isoforms: TAp63 (containing the 5' transactivation domain) and N-terminally truncated (ΔNp63). Additionally, multiple alternative splicing sites produce distinct C-terminal variants. Although previous studies have compared the transcriptomes from HGPS and healthy cells, no differences in TP63 expression were detected. However, isoforms were not distinguished in these prior studies. To determine the isoform expression pattern of TP63 in healthy individuals, RNAseq data derived from the Genotype-Tissue Expression (GTEx) project (GTEx Consortium, Getz, G., et al., Science 348, 648-660 (2015)) was extracted. Samples from GTEx were obtained from tissues of healthy donors and the highest expression of TP63 is detected in the skin. Moreover, isoform specific analysis showed that ΔNp63 are the predominant isoforms expressed in skin tissue.

However, data from GTEx include heterogeneous populations of different cell types within each tissue sample. Hence, microarray data was analyzed from earlier studies comparing transcriptomes in HGPS vs. normal primary fibroblasts (REFS) by extracting only the microarray probes that hybridize specifically to each of the TP63 main isoforms. A slight but significant unbalanced expression of TP63 in HGPS cells was found; specifically, TAp63 is expressed at higher levels than the ΔNp63 isoforms. In contrast, cells derived from healthy donors of similar age displayed balanced expression of both isoforms. To validate these findings in the cells from this study, an isoform-specific expression analysis of TP63 by qRT-PCR was performed. First, expression of progerin was analyzed and high levels of the abnormal protein was confirmed only in HGPS cells. Then, using specific amplicons designed to detect TAp63 and ΔNp63 variants, similar expression levels of both isoforms in fibroblasts derived from young healthy donors was observed. In contrast, TAp63 isoforms are expressed at higher levels than ΔNp63 isoforms in cells derived from HGPS patients. Interestingly, fibroblasts derived from two aged donors (81 and 82 yrs) expressed only TAp63 isoforms, suggesting that alteration in TP63 gene regulation might be also observed in natural aging, through mechanisms that are not associated with early RT. These results demonstrate that abnormal RT of TP63 is correlated with an altered ratio of TP63 variants in the progeroid diseases.

Abnormal TP63 RT is not Dependent on Progerin Expression

The distinct nuclear defects observed in HGPS have been causally linked to the expression of progerin. Moreover, ectopic expression of progerin in normal cells recapitulates the cellular defects observed in HGPS. Hence, whether altered RT of TP63 is dependent on the expression of progerin was analyzed by employing a previously characterized model of inducible progerin (Kubben, N. et al. Cell 165, 1361-1374 (2016); Kubben, N. et al., Methods 96, 46-58 (2016)). First, it was confirmed that overexpression of progerin in normal fibroblasts induced the nuclear alterations observed in HGPS. In accordance with previous studies, induction of progerin altered nuclear envelope structure and increased the number and size of γH2AX foci when compared with the control cell line over-expressing Lamin A. These nuclear alterations, matching the progeria cellular phenotype, are detected at day 2 after progerin induction. Here, RT was analyzed from 0-6 days after induction of progerin in normal fibroblasts and it was found that, despite the nuclear alterations, no significant changes in RT were detected genome wide, including at the TP63 locus, demonstrating that the expression of progerin is not sufficient to alter the temporal order of TP63 replication or create the RT signature identified in HGPS patient cells. These results are, however, consistent with previous findings showing that RT is robust to the depletion of many factors that disrupt chromatin architecture (Dileep, V. et al., Cold Spring Harb. Symp. Quant. Biol. 80, 53-63 (2015)) and underscore the importance of the RT alterations that are not detected in progeroid disease.

Altered RT in Rothmund-Thomson Syndrome (RTS)

Different progeroid diseases resemble the broad phenotype observed during natural aging; however, distinct specific gene mutations are thought to be the cause of each disease. Since the results presented above suggest that early RT of TP63 is not directly linked to progerin expression, fibroblasts from a patient with RTS were analyzed to determine whether altered RT of TP63 is detected in other progeroid diseases. RTS is a distinct progeroid syndrome associated with inactivating mutations of the RECQL4 gene. Interestingly, an RT alteration specific for RTS was found at the RECQL4 locus and it was also found that the RT of TP63 locus is also altered in RTS. In fact, in an unsupervised analysis of RT, cells from RTS patients clustered with those from HGPS, demonstrating that the two progeroid syndromes share many RT abnormalities. These results confirm that abnormal RT of TP63 is not dependent on progerin expression. Moreover, unbalanced TP63 isoform expression in cells from RTS was also observed, confirming altered regulation of TP63 expression is common to these two progeroid diseases.

TP63 Recapitulates its Abnormal RT upon Differentiation of iPSCs

Figure 14A:
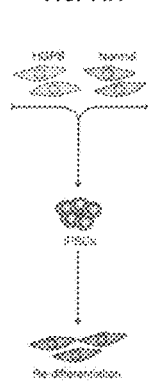
FIG. 14A, 14B, 14C, 14D, 14E, 14F: Altered RT of TP63 is an early marker of progeroid diseases.
Figure 14B:
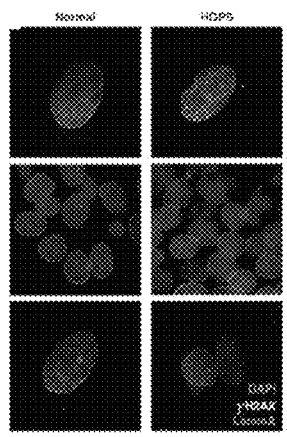
Figure 14C:
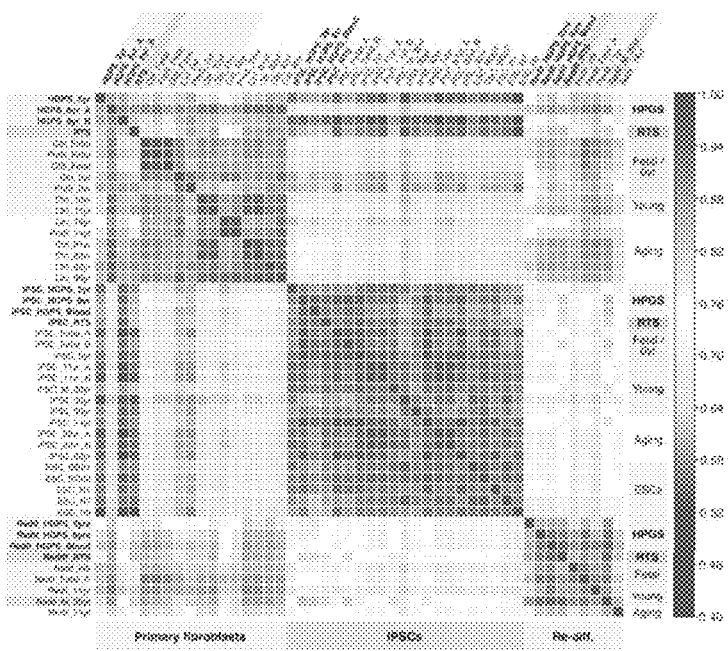

Previously it was shown that cells from aged donors can efficiently generate iPSCs and that the senescent-associated gene expression patterns and metabolism are rejuvenated after re-differentiation. In contrast, although distinct progeria-specific hallmarks (nuclear envelope alterations, γH2AX foci and loss of heterochromatin) are reset in reprogrammed iPSCs, they are reestablished spontaneously upon differentiation back into fibroblasts. Therefore, whether the RT program can be reset in reprogrammed iPSCs derived from progeroid diseases was analyzed (FIG. 14(a)). Consistent with previous studies, iPSCs derived from HGPS showed normal morphology and a decreased signal of γH2AX (FIG. 14(b)). Moreover, very strong genome-wide correlations of RT were found between iPSCs from progeroid diseases (HGPS and RTS) and different human ESC lines as well as with iPSCs derived from fibroblasts of distinct age donors (FIG. 14(c)). Consistently, it was found that the RT program is completely reprogrammed in all iPSCs regardless of the age of the donors or the progeroid diseases (HGPS and RTS). Next, whether the progeroid-specific RT signatures are re-established after re-differentiation of iPSCs was analyzed. First, it was confirmed that a fibroblast-specific RT profile was re-established after re-differentiation of iPSCs. Genome-wide correlations of RT profiles confirmed re-establishment of the fibroblast RT program in all re-differentiated cells (FIG. 14(c)).

Figure 14D:
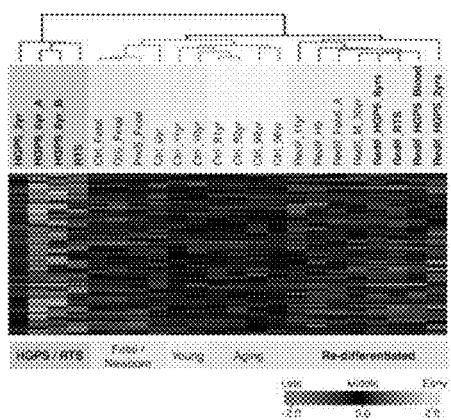
Figure 14E:
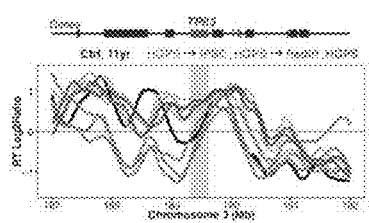
Figure 14F:
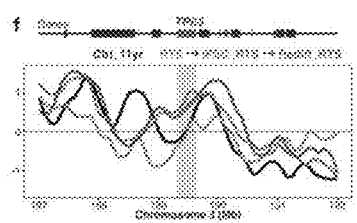
Figure 15A:
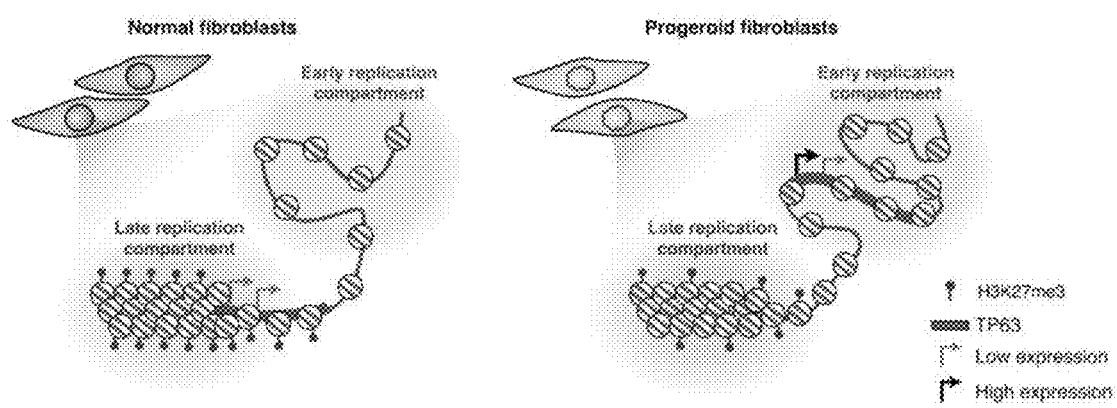
FIG. 15A, 15B: Model of TP63 alterations in progeroid diseases.
Figure 15B:
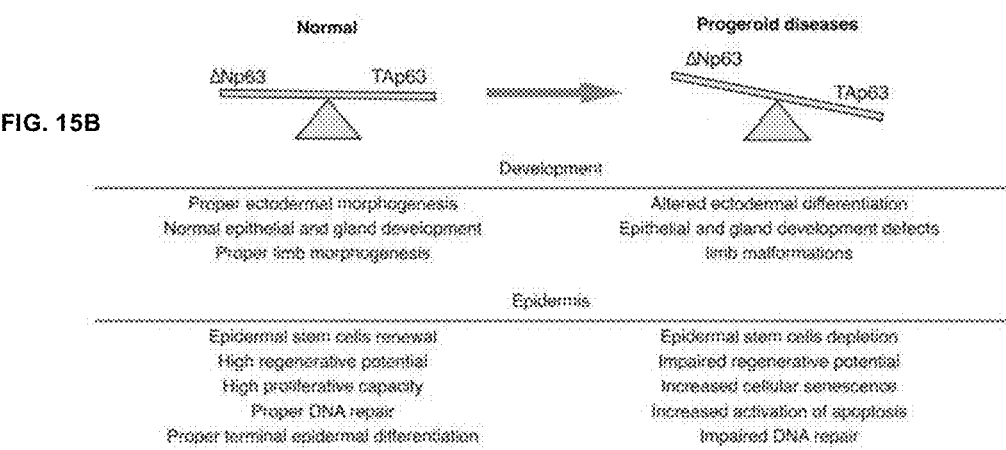

To determine whether the RT abnormalities associated with progeria are reestablished upon re-differentiation of iPSCs, specifically the regions of the "E-progeria" RT signature were examined. Strikingly, unsupervised clustering analysis of the genomic regions within the progeria-specific RT signature demonstrated that HGPS and RTS primary patient samples form a common cluster clearly separated from all normal fibroblasts. In fact, most of the genomic regions from the "E-progeria" RT signature originally identified as HGPS-specific also replicate early in RTS (>75%), confirming that RT alterations at these loci are common to cells from patients with these two different progeroid diseases (FIG. 14(d)). Remarkably, in an unsupervised analysis of RT-variable regions genome wide, HGPS and RTS primary patient samples form a clearly distinct cluster from normal patient samples indicating that these two different progeroid syndromes share common RT abnormalities genome-wide. Moreover, this same genome-wide analysis found that re-differentiated fibroblast cells derived from RTS iPSCs clustered with those from HGPS, demonstrating that the two progeroid syndromes also re-acquire similar RT patterns upon re-differentiation. Interestingly, most of progeria-related RT defects, which are reversed upon reprogramming to iPSCs, were not re-acquired upon re-differentiation to embryonic-like fibroblasts (FIG. 14(d)). However, specific genomic regions had reacquired the progeroid-specific abnormal RT pattern upon re-differentiation (FIG. 14(d)). Among these few loci the TP63 locus re-acquired abnormal early RT very early during re-differentiation (passages 3-4), despite being fully reset to 'healthy', late RT at the pluripotent stage (FIG. 14(e), 14(f)). Moreover, although fibroblasts from the youngest HGPS patient (HGPS_2 yr) clustered with cells from older patients with progeroid diseases (FIG. 14(d)), they showed fewer abnormalities when compared with normal fibroblasts; nevertheless, alterations in TP63 locus are already present in this patient. Thus, these findings suggest that aberrant RT of TP63 is an early developmental marker of progeroid conditions.

RT Changes in TP63 during Normal Human Development

RT is an epigenetic property regulated during development that is linked to cell identity. Moreover, cancer cells show abnormalities in replication patterns that match RT features of other cell lineages, suggesting a loss of normal cell type-specific developmental regulation of the RT program. Hence, it was asked whether the RT alterations at the TP63 locus in progeroid syndromes coincide with regulated changes in RT observed during normal human development. It was found that the TP63 locus is late replicating in human ES cells, changes transiently to early replication during cell fate commitment to all three germ layers and back to late replication in the differentiated cell types of all differentiation pathways analyzed. Moreover, transcriptional induction of TP63 is restricted to early stages of mesodermal differentiation correlated with early replication. Finally, RNAseq data from ENCODE was examined, and it was found that TP63 is expressed in human ESCs and (at lower levels) in fetal and newborn fibroblasts, correlated with enrichment of H3K27me3 in fetal and newborn fibroblasts. Altogether, these results show that early replication of TP63 is a normal epigenetic state of this locus during development, restricted to early stages of cell differentiation when the gene is highly expressed and then switches back to late replication in coordination with epigenetic downregulation of the gene.

This study constitutes the first genome-wide characterization of RT program abnormalities in progeroid diseases and the most comprehensive comparison to natural aging. In contrast to numerous studies linking abnormalities of these congenital disorders to age-related defects, a specific RT signature was identified that distinguishes progeroid syndromes from natural aging (FIG. 12(b)). Also, ontology analysis revealed TP63 among the progeroid-specific RT alterations linked to phenotypic defects characteristic of this family of congenital disorders (FIGS. 12(f) and 13(a)).

Methods

Cell Culture

Primary cells were obtained from the Coriell Institute for Medical Research (NJ, USA), from the Progeria Research Foundation (PRF) and from donors from CHRU Montpellier cohort. Coriell Institute and PRF banks blinds all donor samples with a numerical identification code to ensure privacy and confidentiality. All cells tested negative for mycoplasma by MycoAlert PLUS detection kit (Lonza). Human primary fibroblasts were maintained in Dulbecco's Modified Eagle Medium (DMEM, Invitrogen) containing 10% heat-inactivated Fetal Bovine Serum (FBS, PAA), 2 mM L-Glutamine, 1% penicillin and streptomycin (all from Invitrogen). Human ES cells and iPSCs were maintained on feeder-free culture on matrigel (BD Biosciences) with chemically defined mTeSR (Stemcell technologies) medium, as previously described (Ludwig, T. E. et al. Nat. Methods 3, 637-646 (2006)).

Reprogramming into iPSCs

Primary fibroblasts were reprogrammed to iPSCs either by infection with lentiviral or sendai viral vectors containing reprogramming factors: OCT4, SOX2, KLF4 and C-MYC. Vectors were obtained from Addgene. 293T cell line (Invitrogen) was used to produce transgene-expressing lentiviruses. Human primary fibroblasts were seeded at $2\times10^5$ cells per 35 mm dish one day before transduction. Equal amounts of supernatants containing each lentivirus were mixed, transferred to the fibroblast dish, and incubated overnight. Twenty-four hours after transduction, the lentivirus-containing medium was replaced with the second supernatant. Six days after transduction, fibroblasts were harvested by trypsinization and re-plated in a 100 mm dish on a feeder layer. The next day, medium was replaced with hESCs medium supplemented with 10 ng/ml bFGF. The medium was changed every other day. Thirty to forty days after transduction, colonies were picked and transferred into 35 mm dish on a feeder layer with 2 ml of hESC medium supplemented with 10 ng/ml bFGF.

Re-Differentiation of iPSCs iPSCs were differentiated to fibroblasts as previously described. Briefly, embryoid bodies (cell aggregates of ESCs/iPSCs) were generated in AggreWell™ EB Formation Medium, and supplemented with 0.3 mM ascorbic acid (Sigma-Aldrich), 10 ng/ml transforming growth factor beta2 (TGFβ$_2$) (R&D systems) and ITS-A supplement (diluted as manufacturer's instruction) (Invitrogen) on a low-binding dish. For inducing cell outgrowth, embryoid bodies were attached to a gelatin-coated dish, and cultured in DMEM (with high glucose) (Invitrogen) supplemented with ascorbic acid and 20% bovine serum for 10 days. Cells that grew out from embryoid bodies were passaged and cultured every week to obtain consistent spindle-shaped cells for at least 4 passages.

Immunofluorescence

Cells were grown in coverslips, fixed with 4% paraformaldehyde and permeabilized (PBS/0.5% Triton-X 100). Immunofluorescence detection was performed by a 1 hr incubation in blocking buffer (PBS/0.05% Tween-20, 5% bovine serum albumin), followed by incubation with primary antibodies (mouse-Anti-H2AX Thermo MA1-2022; goat-Anti-LaminB SantaCruz Sc-6217) for 1 hr, two washes in PBS/0.5% Tween-20, 1 hr of incubation with secondary antibodies (Donkey-anti-Mouse-488; Donkey-AntiMouse-Alexa568; Donkey-AntiGoat-Alexa647 from Invitrogen) and DNA was labeled by DAPI staining. Images were collected using a Deltavision microscope (Applied Precision) equipped with a cooled charge-coupled device camera (CoolSNAP HQ, Roper Scientific). 3D images were captured at different stage positions and processed using deconvolution software (SoftWoRx 3.5.0, Applied Precision).

qRT-PCR

Total RNA was extracted with RNeasy (Qiagen), according to the manufacturer's instructions. First-strand cDNA was synthesized with the SuperScript III first-strand synthesis system (Invitrogen). Isoform-specific primers were designed at exon junctions and optimized to have comparable efficiencies. All reactions were performed with FastStart SYBR Green Master (Roche) with ROX. qPCR reactions were tripled and performed in ABI 7500 Fast system through 40 cycles (15 s at 95° C., 45 s at 60° C.). CT values were generated by ABI software and the relative gene expression was calculated by ΔΔCT method using HPRT1 gene as reference.

Genome-Wide RT Profiling

Genome-wide RT profiles were constructed as previously described. Briefly, cells were pulse labeled with BrdU and separated into early and late S-phase fractions by flow cytometry and processed either by Repli-Chip or Repli-Seq. For Repli-Chip, BrdU-substituted DNA from early and late S-phase populations was immunoprecipitated, differentially labeled, and co-hybridized to a whole-genome oligonucleotide microarray. Microarray hybridization and data extraction were performed according to standard procedures recommended by NimbleGen. For Repli-Seq, sequencing libraries of BrdU-substituted DNA from early and late fractions were prepared by NEBNext Ultra DNA Library Prep Kit for Illumina (E7370). Sequencing was performed on Illumina-HiSeq 2500 by 50 bp single end. Reads of quality scores above 30 were mapped to Hg19 reference genome using bowtie2. Approximately 7 million uniquely mapped reads were obtained from each library. Read counts were binned into 5 kb non-overlapping windows, and log 2 ratios of read-counts between early and late fractions were calculated.

Clustering Analysis

Significant RT variable regions were defined as those regions with differences ≥1 in pairwise comparisons between all samples analyzed. Unsupervised hierarchical and k-means clustering analysis were performed using Cluster 3.0 (de Hoon, M. J. L. et al., Bioinformatics 20, 1453-1454 (2004)) using un-centered correlation metrics and average linkage. Heatmaps and dendrograms were generated in JavaTreeView.

Data Availability

All datasets generated in this study are deposited in the NCBI Gene Expression Omnibus database (GEO).

Code Availability Repli-Chip and Repli-Seq analysis was performed in R. RT datasets were normalized using the limma package in R and re-scaled to equivalent ranges by quantile normalization. Correlation analysis was performed using the corrplot package in R. Detailed computational pipeline for genome-wide measurement of RT has been published elsewhere (Ryba, T. et al., Nat Protoc 6, 870-895 (2011); Marchal, C. et al. Repli-seq: genome-wide analysis of replication timing by next-generation sequencing. (2017). doi:10.1101/104653)).

Example 3

Stability of Patient-Specific Features of Altered DNA Replication Timing In Xenografts of Primary Human ALL A major impediment to studies of RT in human ALLs has been the usually low frequency of dividing cells in fresh or cryopreserved patients' samples. In addition, conditions that support or stimulate ALL cell survival and proliferation ex vivo are generally lacking or poorly understood. Genetically engineered mouse models of human leukemia offer an experimental alternative, but these face the same cell growth problems and rarely recapitulate the genetic complexity associated with the clinical examples of the human leukemias they are intended to model. A more promising alternative is afforded by the use of highly immunodeficient mice transplanted with primary patient-derived ALL cells where retention of many characteristics of the initial leukemia cells, including their patterns of dissemination, organ infiltration, and immunophenotypic, and genomic stability have been demonstrated. Genomic analysis of such patient-derived xenografts (PDXs) has also been useful in revealing their subclonal architecture and evolution.

In the studies described herein, the feasibility of analyzing the RT profiles of human ALL cells before and after serial passaging as PDXs was demonstrated. The results reveal stability in both their patient- and subclone-specific RT profiles.

Herein are reported the results for samples from 8 additional ALL patients, 5 of which were also examined after passage and expansion in mice. The RT profiles obtained confirm their disease and patient specificity and further demonstrate their preservation in the derived PDXs. These results thus establish RT as a stable epigenetic property of patient-derived ALL cells that is retained after many cell divisions.

The PDXs derived from B-ALL #4 showed subclone-specific differences in the RT signatures obtained from the cells harvested from different passages of PDXs. In this example, the RT profile of the second passage PDX mirrored that of the primary sample, but the first and third PDXs were different and similar to one another. Tracking CNVs within these same cells revealed a picture of alternating dominant subclones derived from the same patient. This dynamic is similar to a previously reported example of a serially passaged B-ALL in which CNV data also showed that a subclone not initially detectable in the patient's original sample emerged in the first PDX, and was then followed by re-emergence of the CNV pattern in the original cells in a second passage PDX. It is also similar to data reported for adult AML or colon cancer using Southern blots to track the changing growth dynamics of subclones identified by retroviral insertion sites. Similar data has also been reported for genetically defined or DNA-barcoded subclones tracked in PDXs derived from primary samples of human breast cancer or de novo generated human breast cancers. Taken together, these results demonstrate that RT profiles are a stable epigenetic property of these subclones throughout their dynamic fluctuations and underscore the promise of DNA RT of PDXs as a new and promising approach to elucidate the subclonal dynamics that underpin the variable evolution and progression of human ALLs and possibly other human malignancies as and the mechanisms driving these changes.

Example 4

Using RT Signature Methods to Identify Additional Disease Markers

Figure 16A:
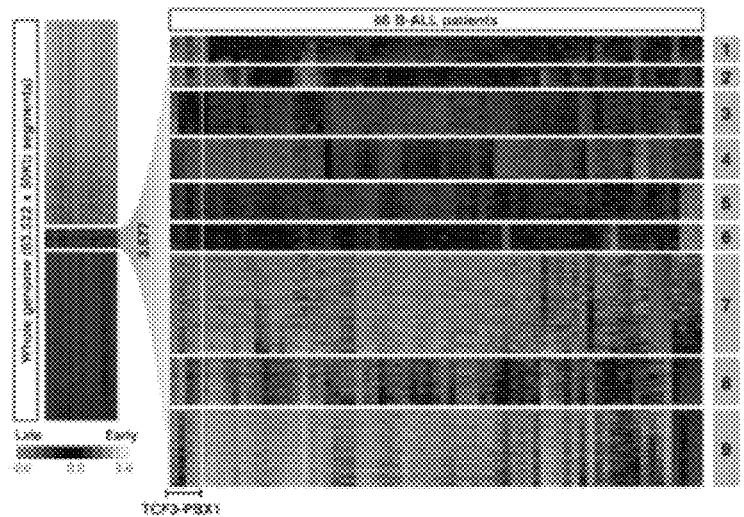
FIGS. 16A, 16B, 16C, 16D: Identifying RT Signatures and Comparison to Normal Cell Types.
Figure 16B:
Figure 16C:
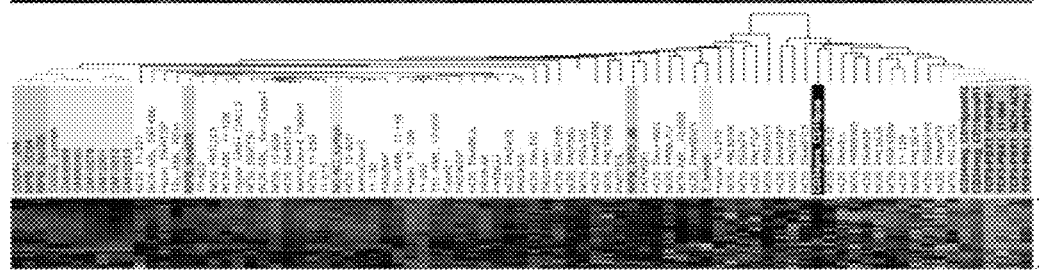
Figure 16D:
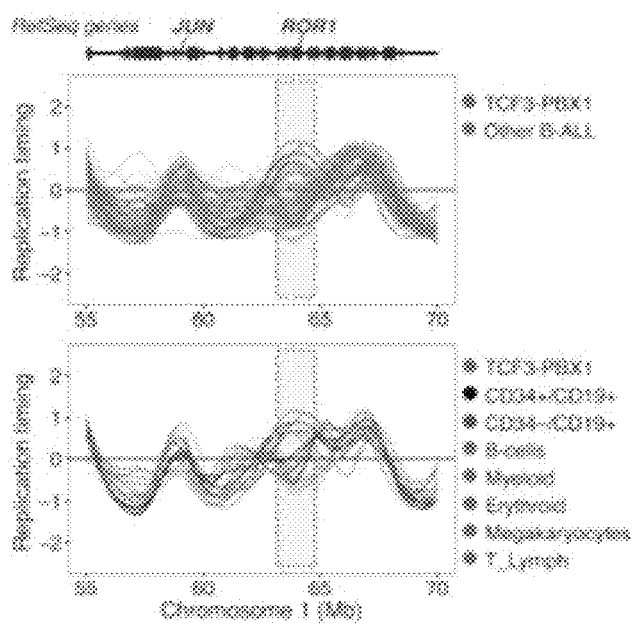

FIG. 16A-16D illustrates the pipeline developed to stratify patient BCP-ALL RT profiling data. RT signatures are first identified by unsupervised K-means clustering of all 50 kb genomic segments that show significant variation between samples (Rivera-Mulia, J. C. et al. Dynamic changes in replication timing and gene expression during lineage specification of human pluripotent stem cells. Genome Res, doi:gr.187989.114 [pii] 10.1101/gr.187989.114 (2015)). Using this approach, several BCP-ALL RT signatures have been identified that are enriched in genes that are transcribed during normal hematopoiesis and/or are mis-regulated in leukemia, including RUNX1, an essential HSC transcription factor also commonly rearranged in pediatric leukemia, and BCL11B (B-cell CLL/lymphoma 11B) that is involved in regulating T-versus B-cell fates and has been linked to T-ALL. Two signatures were identified (#1 and #2 in FIG. 16A) common to all patients exhibiting the t(1;19) translocation (including an established cell line). These signatures also appeared in samples from patient-derived xenografts (PDXs) established from a TCF3-PBX1 patient's cells. These TCF3-PBX1-specific RT signatures were enriched in PBX1 binding sites, suggesting that these RT signatures are linked to the t(1;19) translocation and/or TCF3-PBX1 expression. One signature was also found (#3) that sub-stratified these same patients and may have prognostic associations (FIG. 16A). For each BCP-ALL RT signature, a hierarchical clustering analysis is performed of all leukemia samples together with all normal hematopoietic cell types to identify RT features within each RT signature that match or deviate from those seen in normal hematopoietic cells. FIG. 16B shows a preliminary example of such a clustering for RT signature #1, revealing several NOS (Not Otherwise Specified; no prognostic genetic markers) BCP-ALL samples that share this signature. This clustering also reveals a subset of features within Signature #1 that are shared with normal pre-B cells but not normal pro-B or mature B cells (indicated with a bracket in FIG. 16B). Interestingly, many of these same features emerge as the most statistically significant features distinguishing TCF3-PBX1 from other BCP-ALL subtypes in a supervised comparison using a stringent Monte-Carlo-based algorithm that was developed (Ryba et al., Genome Res 22, 1833-1844 (2012)). When the unsupervised hierarchical clustering was repeated using only this subset of features (FIG. 16C), TCF3-PBX1 BCP-ALL clustered tightly with pre-B cells. This subset of features includes the gene for the receptor orphan tyrosine kinase receptor 1 (ROR1). ROR1 is highly expressed on t(1;19) pre BCP-ALL blasts and required for their viability, even though ROR1 is not directly regulated by either the TCF3-PBX1 fusion protein or the pre-B cell receptor (pre-BCR). These results demonstrate the feasibility of the methods described herein to identify biologically relevant features of the RT program that match and deviate from those of normal hematopoietic subsets.

Other Embodiments

Any improvement may be made in part or all of the method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:
1. A method of identifying a cell type or cell types in a test sample of cells or plurality of test samples of cells by identifying a replication timing (RT) signature for the test sample of cells or plurality of test samples of cells, the method comprising:

a) generating a RT profile for the test sample or RT profiles for the plurality of test samples wherein each RT profile is a log 2 ratio of signals from early and late S-phase fractions calculated in non-overlapping windows of 50-200 kb;
b) generating RT profiles for a plurality of reference samples of distinct known cell types, wherein each RT profile is a log 2 ratio of signals from early and late S-phase fractions calculated in non-overlapping windows of 50-200 kb;
c) removing pericentromeric and subtelomeric regions to remove large repetitive DNA regions from the test sample and reference sample RT profiles;
(d) removing chromosome segments having invariant RT between the test and reference samples resulting in a collection of remaining chromosome segments that include all variation in RT between the test and reference samples, wherein the remaining chromosome segments are variant regions;
(e) performing k-means clustering of the variant regions from step (d) and identifying groups of genomic regions that are non-overlapping windows of 50-200 kb with correlated RT patterns across all test and reference samples;
(f) performing unsupervised hierarchical clustering of the test and reference samples from step (e) to construct a dendrogram that groups the test and reference samples in distinct branches, and identifying RT signatures for the test sample or plurality of test samples, wherein each RT signature is a k-means cluster identified in step (e) with an RT pattern specific for the dendrogram branch of the hierarchical clustering that groups the test sample or plurality of test samples; and
(g) identifying the cell type of the test sample or plurality of test samples by establishing to which hierarchical clustering branch the test sample or plurality of test samples belong, wherein clustering of the test sample or plurality of test samples within the same branch of reference samples of a specific known cell type indicates that the identity of the test sample or plurality of test samples is the specific known cell type.

2. The method of claim 1, wherein sex chromosomes are removed in step c) to discard gender differences.

3. The method of claim 1, wherein the specific k-means clusters are those that replicate either earlier or later in the test samples or plurality of test samples as compared with the at least one reference sample.

4. The method of claim 1, wherein the RT signature specific for the test sample of cells or plurality of test samples of cells identifies a set of chromosome regions whose RT distinguishes the test sample of cells or plurality of test samples of cells.

5. The method of claim 1, further comprising identifying a particular disease by identifying the RT signatures for the test sample of cells or plurality of test samples of cells identified in step (f) as RT signatures specific for diseased cells as compared to at least one reference sample obtained from at least one individual not having the particular disease.

6. The method according to claim 1, wherein the plurality of reference samples are available in a public database.

7. The method according to claim 1, wherein the test sample of cells or plurality of test samples of cells is not pre-defined.

8. The method according to claim 1, wherein RT profiles are generated for genomes or sub-genomic regions.

9. The method according to claim 1, wherein the test sample of cells or plurality of test samples of cells are frozen banked cells that have been cultured and expanded in patient-derived xenografted mice.

10. The method according to claim 1, wherein generating a RT profile comprises at least one of: array hybridization, sequencing, S/G1, and E/L.

11. The method according to claim 1, wherein the test sample of cells or plurality of test samples of cells are human cells.

* * * * *